US007521567B2

(12) United States Patent
Fujiwara et al.

(10) Patent No.: US 7,521,567 B2
(45) Date of Patent: Apr. 21, 2009

(54) AMINE COMPOUND AND USES THEREOF

(75) Inventors: Makoto Fujiwara, Okayama (JP); Natsuko Sonoda, Okayama (JP); Makoto Satsuki, Okayama (JP); Sadaharu Suga, Okayama (JP); Hisayoshi Fujikawa, Aichi (JP); Koji Noda, Aichi (JP); Yasunori Taga, Aichi (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 251 days.

(21) Appl. No.: 10/564,039

(22) PCT Filed: Jul. 7, 2004

(86) PCT No.: PCT/JP2004/009660

§ 371 (c)(1),
(2), (4) Date: Jan. 10, 2006

(87) PCT Pub. No.: WO2005/005408

PCT Pub. Date: Jan. 20, 2005

(65) Prior Publication Data

US 2006/0226421 A1 Oct. 12, 2006

(30) Foreign Application Priority Data

Jul. 11, 2003 (JP) .............................. 2003-273687
Mar. 3, 2004 (JP) .............................. 2004-059280

(51) Int. Cl.
C07D 311/02 (2006.01)
H01J 1/62 (2006.01)
H01L 29/08 (2006.01)

(52) U.S. Cl. .......................... 549/283; 313/504; 257/40
(58) Field of Classification Search ................ 549/283; 313/504; 257/40
See application file for complete search history.

(56) References Cited

FOREIGN PATENT DOCUMENTS

| JP | 54-151024 A | 11/1979 |
|---|---|---|
| JP | 57088455 | * 11/1980 |
| JP | 57-88455 A | 6/1982 |
| JP | 58-29803 A | 2/1983 |
| JP | 59-56403 A | 3/1984 |
| JP | 63-23901 A | 2/1988 |
| JP | 64-33103 A | 3/1989 |
| JP | 06-3291 A | 1/1994 |
| JP | 06-122874 A | 5/1994 |
| JP | 06-329654 A | 11/1994 |
| JP | 11-247449 | * 9/1999 |
| JP | 2001-76875 A | 3/2001 |
| JP | 2001-76876 A | 3/2001 |
| JP | 2001-329257 A | 11/2001 |
| JP | 2002-226484 A | 8/2002 |
| JP | 2003-249371 A | 9/2003 |
| JP | 2003-249372 A | 9/2003 |
| JP | 2004-6222 A | 1/2004 |

OTHER PUBLICATIONS

Bader et al. Proceedings of SPIE-The international Society for Optical Engineering, 2001, vol. 4461, pp. 304-310.*
Bader, M. et al., "Design and Synthesis of New Acceptor Molecules for Photo-Induced Electron Transfer Reverse Saturable Absorption", *Proceedings of SPIE-The International Society for Optical Engineering*, vol. 4461, pp. 304-310, 2001.

* cited by examiner

*Primary Examiner*—D. Margaret Seaman
*Assistant Examiner*—Nizal S Chandrakumar
(74) *Attorney, Agent, or Firm*—Browdy and Neimark, P.L.L.C.

(57) ABSTRACT

The objectives of this invention are to extend the range of choosing materials to use in the preparation of photopolymerizable compositions by providing a novel organic compound which absorbs a visible light; or to provide an organic material which is useful as host compound in organic electroluminescent devices, as well as its uses: The objectives are attainable by providing an aromatic tertiary amine compound bearing within the same molecule one or more specific atomic groups, a luminescent agent directed to use in organic electroluminescent devices comprising it, and an organic electroluminescent device using such amine compound, as well as its uses.

2 Claims, 3 Drawing Sheets

AMINE COMPOUND AND USES THEREOF

TECHNICAL FIELD

This invention relates to a novel amine compound and its uses.

BACKGROUND ART

In this age of the growing importance of information, photochemical polymerization is now usually used in various fields, extending its application to the field of information storage and electronic circuit such as holography, lithographic plate for printing and printed- or integrated-circuit beyond the field of synthetic resin. Photochemical polymerization is a technique to bring polymerizable compounds into polymerization by light irradiation, which can be roughly classified into photopolymerization where polymerization is initiated by directly irradiating a photopolymerizable compound to activate it, and photosensitizing polymerization where a polymerizable compound is brought into polymerization by irradiating it in the presence of a photosensitizer to form active species of the photosensitizer. Each photochemical polymerization is characterized in that the initiation and termination of polymerization can be controlled by starting and stopping an exposing light source, as well as in that the degree and rate of polymerization can be easily controlled by selecting the strength and wavelength of the light source. Further, photochemical polymerization proceeds even at a reduced temperature because it usually does not require so much energy for initiating polymerization. In the field of information storage such as holography and lithographic plate for printing, there is an increasing demand for photopolymerizable compositions which are polymerizable by irradiating them with a visible light such as the second harmonic of argon ion laser, helium ion laser, and Nd-YAG laser because of these advantages of photochemical polymerization.

Since many polymerizable compounds and polymerization initiators to be incorporated in photopolymerizable compositions absorb only ultraviolet ray, photosensitizers become one of key techniques in case that such a photopolymerizable composition is brought into polymerization with a visible light. The properties required for polymerization initiators are to be large in molecular absorption coefficient, capable of sensitizing various polymerizable compounds and polymerization initiators, high in sensitization efficiency, superior in solubility in solvents, mixing ability to other ingredients and stability. Typical organic compounds having a photosensitizing ability are, for example, melocyanine dyes disclosed in Japanese Patent Kokai No. 151,024/79, cyanine dyes disclosed in Japanese Patent Kokai No. 29,803/83, stilbene dyes disclosed in Japanese Patent Kokai No. 56,403/84, coumarin derivatives disclosed in Japanese Patent Kokai No. 23,901/88, methylene blue derivatives disclosed in Japanese Patent Kokai No. 33,103/89, and pyran derivatives disclosed in Japanese Patent Kokai No. 329,654/94, all of which however bear both merits and demerits: There have been found no substances which consistently exhibit the above-described properties in photopolymerizable compounds containing polymerizable compounds, polymerization initiators and binding resins. Thus, for example, in the field of information storage and electric equipment which are new application fields of photochemical polymerization, one first chooses several materials such as polymerizable compounds and binders which may meet to the final uses other than photosensitizers, then screens through trial and error a variety of organic compounds which may suit to the polymerizable compounds and polymerization initiators.

By the way, in the field of information displays, organic electroluminescent device (abbreviated as "organic EL device" hereinafter) has been highlighted as displaying device of the next generation. Currently, cathode-ray tube is predominantly used in information displaying equipments in larger sizes such as computer terminals and television sets. Cathode-ray tube is however large in both volume and weight and high in operation voltage, thus it may be unsuitable in portable equipments. More required is an information displaying equipment which is in a thinner and lighter panel form and operable with a lower voltage and less power consumption. At present, liquid crystal device is extensively used in various fields because of the merit that it is operable with a lower voltage and less power consumption. Liquid crystal device, however has the demerits that one can hardly receive a clear information therefrom when one view it at an angle outside the specific ranges, as well as that its power consumption is not so low as expected because it usually requires backlight. Organic EL device has been proposed as displaying device which may overcome the above demerits.

Organic EL device is a light-emitting device that utilizes a luminescence such as fluorescence or phosphorescence: It usually comprises a luminescent layer incorporated with a luminescent compound and inserted between a cathode and anode to which dc voltage is energized to inject holes and electrons in the luminescent layer so that a pair of hole and electron recouple each other to make in the luminescent compound an excited state which subsequently returns to the ground state to emit such a luminescence. Organic EL device is characterized in that its luminescent color tint can be controlled to a desired level by choosing an appropriate organic compound to be used as host compound in forming a luminescent layer, and screening a guest compound (or dopant) which may most suit to the host compound. Further, luminescent brightness and life expectancy may be remarkably enhanced, dependently upon the combination of host- and guest-compounds. Organic EL device has been deemed to be excellent in principle because of the merit that it emits a light in an autonomous manner and this would advantageously save power consumption.

Among luminescent compounds proposed hitherto, for example, those which have a coumarin skeleton have the merit that they are very safe and handleable with no special cares in organic EL devices because coumarin is a naturally occurring substance. Many conventional coumarin derivatives however exhibit a prescribed electroluminescence only when used in combination with host compounds, for example, quinolinol metal complexes, resulting in the problem that organic EL devices which may be practically useful with no obstructions can be hardly prepared by forming their luminescent layer with conventional coumarin alone or in combination with a guest compound.

DISCLOSURE OF INVENTION

In view of such a situation, the objectives of this invention are to extend the range of choosing materials to use in the preparation of photopolymerizable compositions by providing a novel organic compound which absorbs a visible light; or to provide an organic material which is useful as host compound in organic EL devices, as well as its uses.

Further in view of such a situation, the present inventors researched and screened aromatic tertiary amines, resulting in the finding that an amine compound bearing within the same molecule one or more atomic groups represented by General Formula 1 is very useful as light-absorbing or luminescent agent in a variety of fields which require organic compounds with such properties because it gives an absorption maximum in the visible region and efficiently absorb a visible light, as well as because such an amine compound usually has a luminescent maximum in the visible region and a satisfiable stability, and emits a visible light when excited. Also was found that such amine compound emits a visible light with an elevated brightness when applied to organic EL devices as luminescent layer material such as host- or guest-compound, as well as that the emission consistently prolongs over a long period of time at ambient temperature.

General Formula 1:

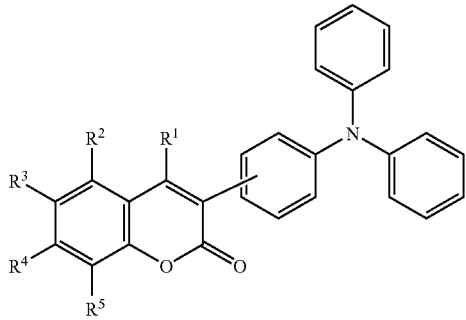

(In General Formula 1, $R^1$ to $R^5$ denote a hydrogen atom or substituent independent of each other.)

Thus, this invention attains the above objectives by providing an amine compound bearing within the same molecule one or more atomic groups represented by General Formula 1.

Further, this invention attains the above objectives by providing a luminescent agent directed to use in organic EL device, said agent comprising an amine compound bearing within the same molecule one or more atomic groups represented by General Formula 1.

Further, this invention attains the above objectives by providing an organic EL device which uses an amine compound bearing within the same molecule with one or more atomic groups represented by General Formula 1.

Further, this invention attains the above objectives by providing a display panel using such organic EL device.

Further, this invention attains the above objectives by providing an information displaying equipment using such organic EL device.

This invention is based on the creation of a novel aromatic tertiary amine compound and the discovery of its industrially useful properties. The amine compound of this invention would find a variety of uses as light absorbing or luminescent agent in various fields of, for example, photochemical polymerization, solar cell, optical filter, dyestuff, dye laser and analysis which require an organic compound with such properties because it has an absorption maximum in the visible region and efficiently absorbs a visible light, as well as because such an amine compound usually has a luminescent maximum in the visible region and a satisfactory stability, and emits a visible light when excited. In addition, the amine compound of this invention is very useful as luminescent agent in organic EL devices because it is formable into a stable membrane and large in thermal stability when in a glass state. Further, the amine compound of this invention is useful as material to modify the chromaticity of luminescence in organic EL devices because it has an absorption maximum in the visible region and a large molecular absorption coefficient. Since the organic EL device using the amine compound of this invention is superior in luminescent efficiency and durability, it is very useful in illuminants in general, as well as in a variety of information displaying equipments, for example, those in panel form which are to visualize information such as those in images and words.

BRIEF DESCRIPTION OF DRAWINGS

In FIG. 1, the reference numeral 1 represents a substrate; 2, an anode; 3, a hole injection/transportation layer; 4, a luminescent layer; 5, an electron injection/transportation layer; and 6, a cathode.

In FIG. 2, the reference numeral 10 represents a substrate; 14, an anode; 16, a hole injection/transportation layer; 18, a luminescent layer; and 20, a cathode.

In FIG. 3, the reference numeral 30 represents a dc source; 32 and 34, voltage-elevating circuits; 36 and 46, driving circuits; 38, a microcomputer; 38a, an I/O; 38b, a ROM; 38c, a RAM; 38d, a CPU; 40, a clock pulse-generating circuit; 42 and 44, oscillating circuits; and 48, a display panel.

PREFERRED EMBODIMENT FOR CARRYING OUT THE INVENTION

Figure 1:
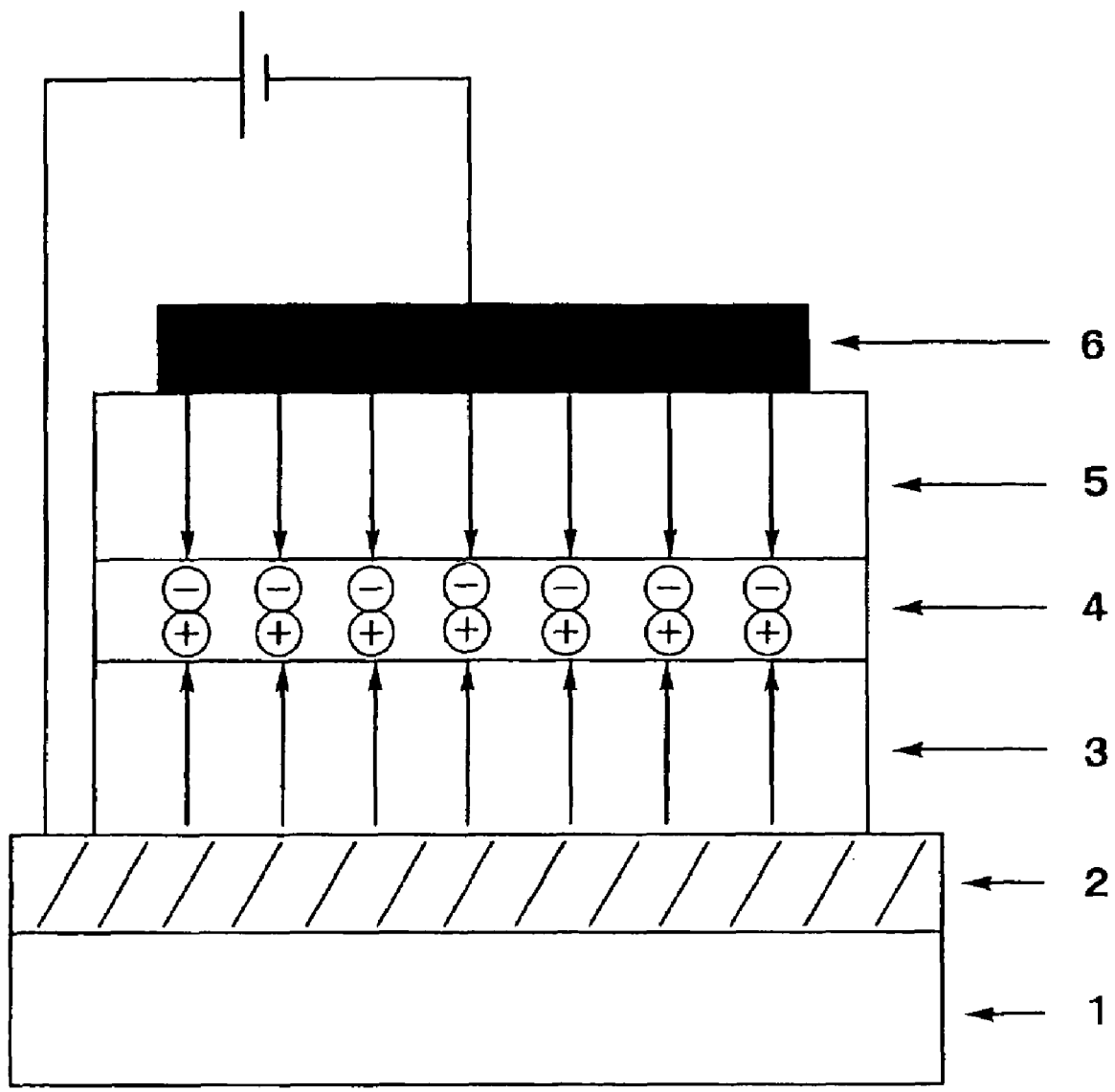
FIG. 1 is a brief figure of an example for organic EL device according to this invention.

As mentioned heretofore, this invention relates to an amine compound bearing within the same molecule one or more atomic groups represented by General Formula 1, as well as to its uses.

General Formula 1:

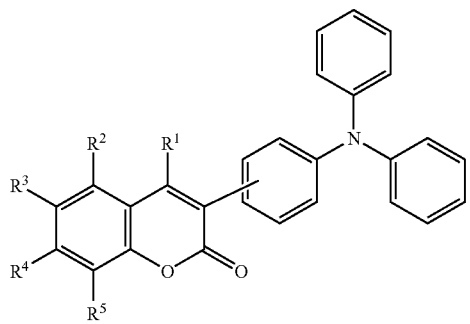

In General Formula 1, $R^1$ to $R^5$ denote a hydrogen atom or substituent independent of each other. The substituents in $R^1$ to $R^5$ are, for example, aliphatic hydrocarbon groups such as methyl, ethyl, propyl, isopropyl, isopropenyl, 1-propenyl, 1-propynyl, 2-propenyl, butyl, isobutyl, sec-butyl, tertThutyl, 2-butenyl, 1,3-butadienyl, pentyl, isopentyl, neopentyl, tert-pentyl, 1-methylpentyl, 2-methylpentyl, 2-pentenyl, 2-penten-4-ynyl, hexyl, isohexyl, 5-methylhexyl, heptyl, octyl, nonyl, decyl, and dodecyl groups; alicyclic hydrocarbon groups such as cyclopropyl, cyclobutyl, cyclopentyl, cyclopentenyl, cyclopentadienyl, cyclohexyl, cyclohexenyl, cyclohexadienyl, cycloheptyl, cyclooctyl, and cyclooctadienyl groups; aromatic hydrocarbon groups such as phenyl, o-tolyl, m-tolyl, p-tolyl, xylyl, mesityl, o-cumenyl, m-cumenyl, p-cumenyl, biphenylyl, naphthyl, anthryl, phenalenyl, phenanthryl, and pyrenyl groups; ether groups such as methoxy, ethoxy, propoxy, isopropoxy, butoxy, isobutoxy, sec-butoxy, tert-butoxy, pentyloxy, isopentyloxy, hexyloxy, aryloxy, phenoxy, and naphthyloxy groups; ester groups such as methoxycarbonyl, ethoxycarbonyl, propoxycarbonyl, acetoxy, and benzoyloxy groups; amino groups such as methylamino, dimethylamino, ethylamino, diethylamino, propylamino, dipropylamino, isopropylamino, diisopropylamino, butylamino, dibutylamino, isobutylamino, diisobutylamino, sec-butylamino, tert-butylamino, pentylamino, dipentylamino, hexylamino, cyclohexylamino, piperidino, phenylamino, N,N-diphenylamino, naphthylamino, N,N-naphthylphenylamino, N,N-dinaphthylamino, and N-carbazolyl groups; halogen groups such as fluoro, chloro, bromo, and iodo groups; hydroxy group; carboxy group; cyano group; nitro group; and combinations thereof.

When $R^2$ to $R^5$ are substituents, the neighboring two of them may couple each other to form a cyclic structure, for example, benzene, naphthalene, anthracene, phenanthrene, piperidine, pyrrolidine, morpholine, or julolidine ring, including the carbon atoms to which the neighboring two substituents are linked. In this case, $R^2$ to $R^5$ apparently do not exist as independent substituents.

Examples of the amine compound according to this of the amine compound according to this invention are those represented by Chemical Formulae 1 to 50. Each compound has an absorption maximum at a wavelength around 300 to 500 nm, usually, 400 to 470 nm and a large molecular absorption coefficient ($1\times10^4$ or larger, particularly, $3\times10^4$ or larger) at the absorption maximum wavelength (a molecular absorption coefficient at an absorption maximum wavelength will be abbreviated as "$\epsilon$" hereinafter), and as a result efficiently absorbs a light in the wavelength region. The amine compounds represented by Chemical Formulae 1 to 50 have a luminescent maximum such as fluorescence maximum at a wavelength around 500 to 650 nm, releasing a luminescence in the green to red region when excited. The amine compound of this invention usually has a decomposition point exceeding 400° and a glass transition point of 110° or higher. As well known, the decomposition point and glass transition point in organic compounds have been deemed to be a characteristic of their thermal stability: Organic compounds with higher decomposition and glass transition points are larger in thermal stability. Because of these, the amine compound of this invention is very useful in the field of organic EL devices which require luminescent organic compounds with a superior thermal stability. Both decomposition and glass transition points of the amine compound according to this invention can be determined by conventional differential scanning calorimetry analysis (abbreviated as "DSC analysis" hereafter).

The amine compound of this invention shall not be restricted to those which bear within the same molecule only one atomic group represented by General Formula 1: It may be those which as seen in, for example, Chemical Formulae 23 to 31, 33, 34, 37, 38, and 44, bear within the same molecule two or more atomic groups represented by General Formula 1, as well as those where in the atomic groups represented by General Formula 1, a part or whole benzene rings which are bound to the nitrogen atom to form a tertiary amine group is further bound with one or more substituents similar to those in $R^1$ to $R^5$, or allowed to share a part of condensed polycyclic aromatic hydrocarbon groups or heterocyclic groups. In particular, the amine compound of this invention, which bears a plurality of coumarin residues within the same molecule, is characterized in that it is significantly higher in light absorbing- and light emitting abilities than those bearing only one coumarin residue. In the atomic groups represented by General Formula 1, the coumarin residue may be bound to a benzene ring in the triphenylamino group at the site of ortho, meta, or para position against the nitrogen atom in the tertiary amino group: However, in usual case, the para position is preferred with respect to synthetic viewpoints such as the availability of starting materials and yield for objective amine compounds.

Chemical Formula 1:

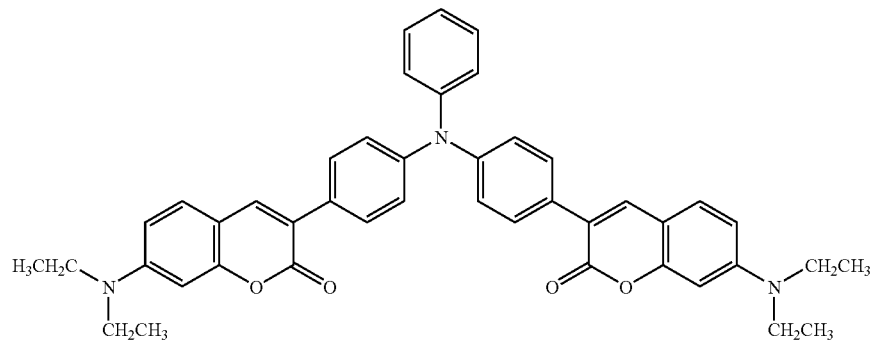

-continued
Chemical Formula 2:
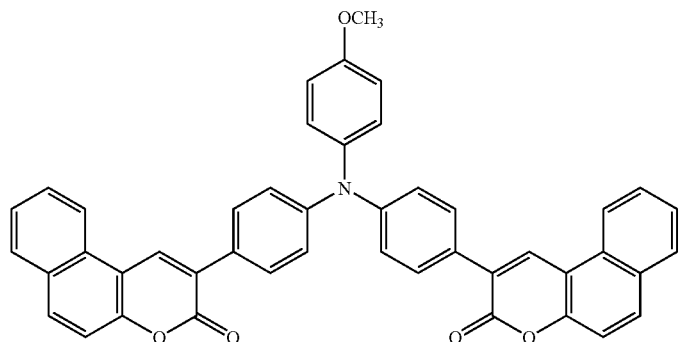
Chemical Formula 3:
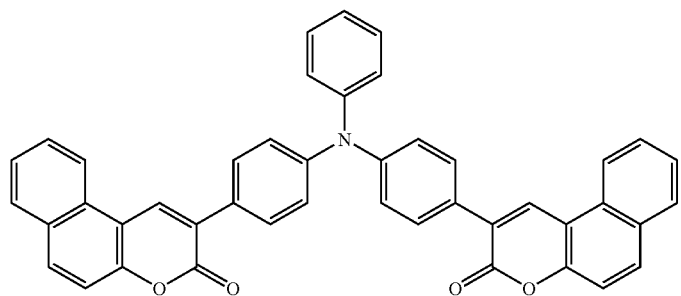
Chemical Formula 4:
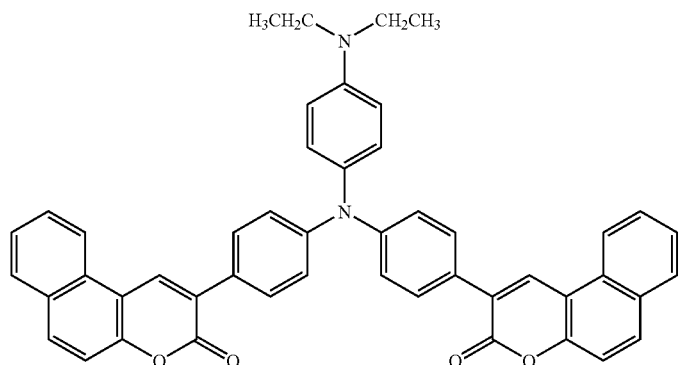
Chemical Formula 5:
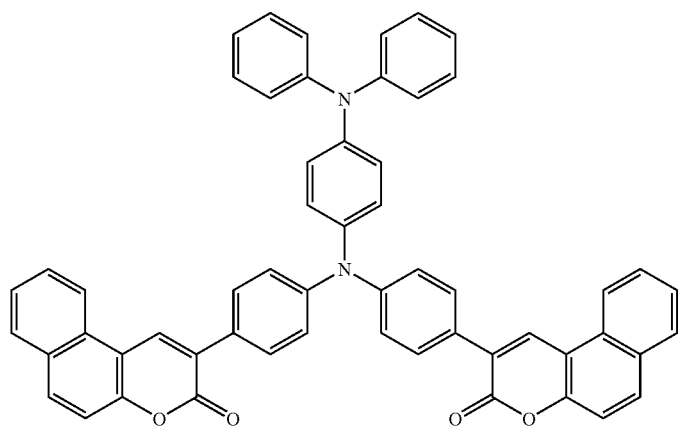

-continued
Chemical Formula 6:
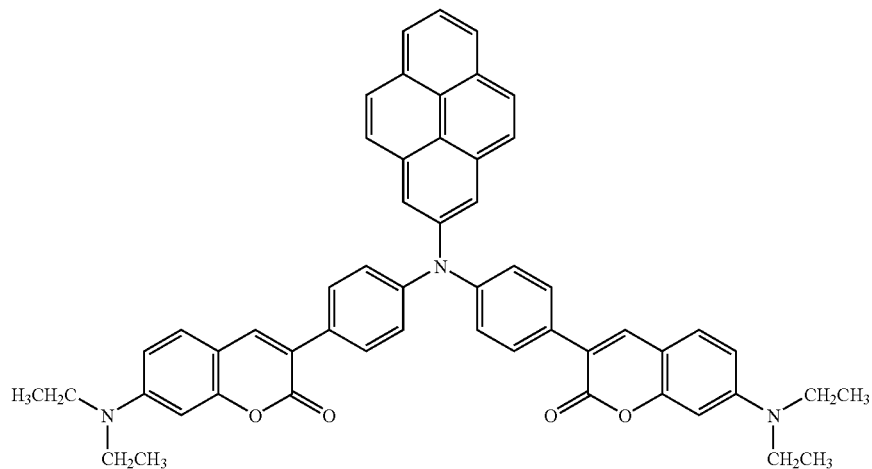
Chemical Formula 7:
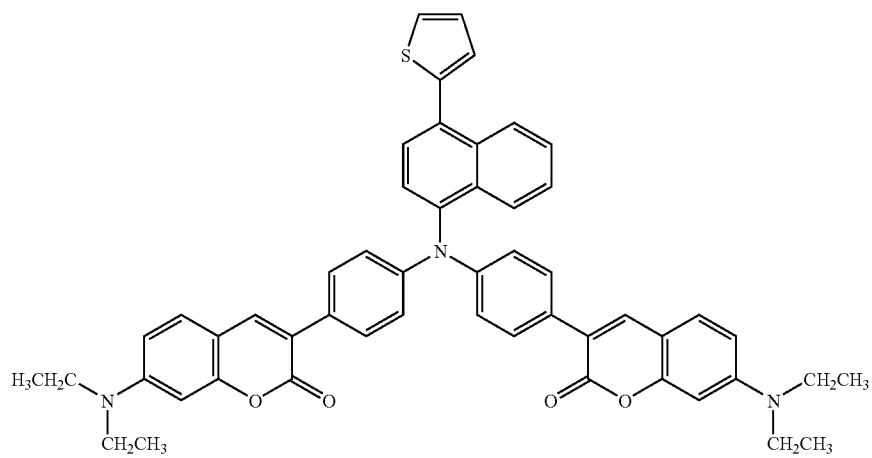
Chemical Formula 8:
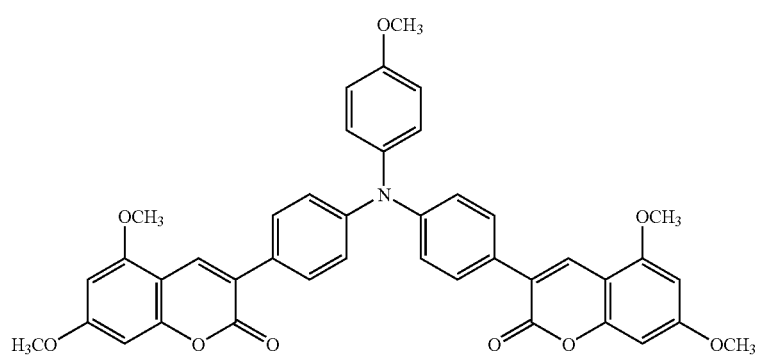

Chemical Formula 9:
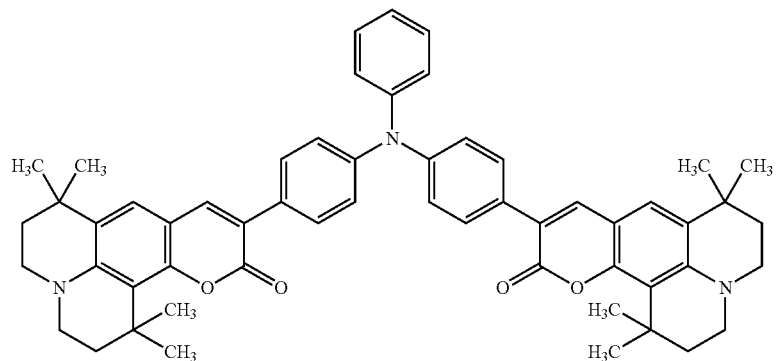
Chemical Formula 10:
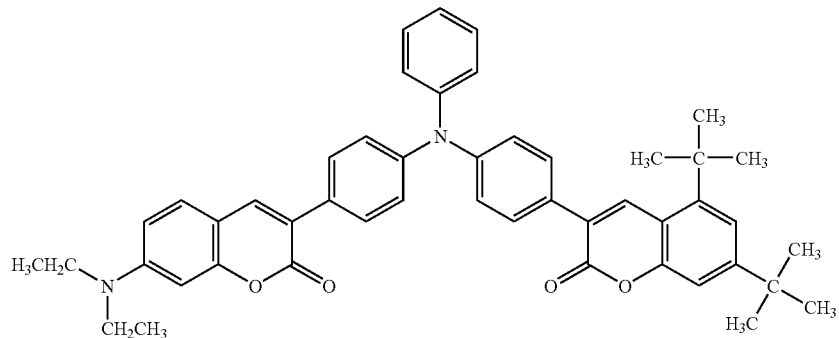
Chemical Formula 11:
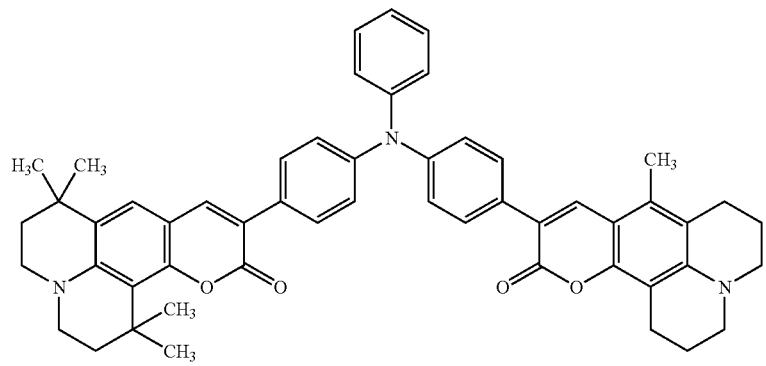

-continued
Chemical Formula 12:
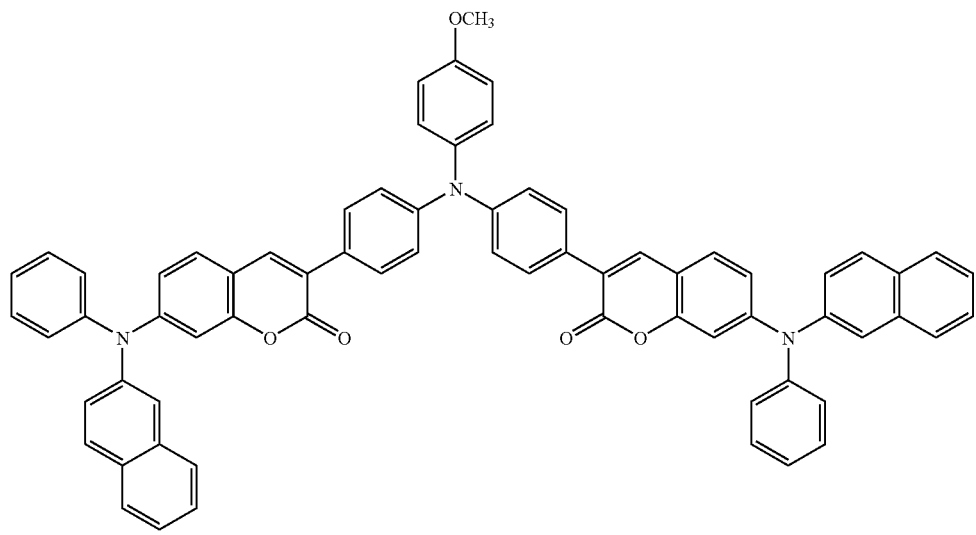
Chemical Formula 13:
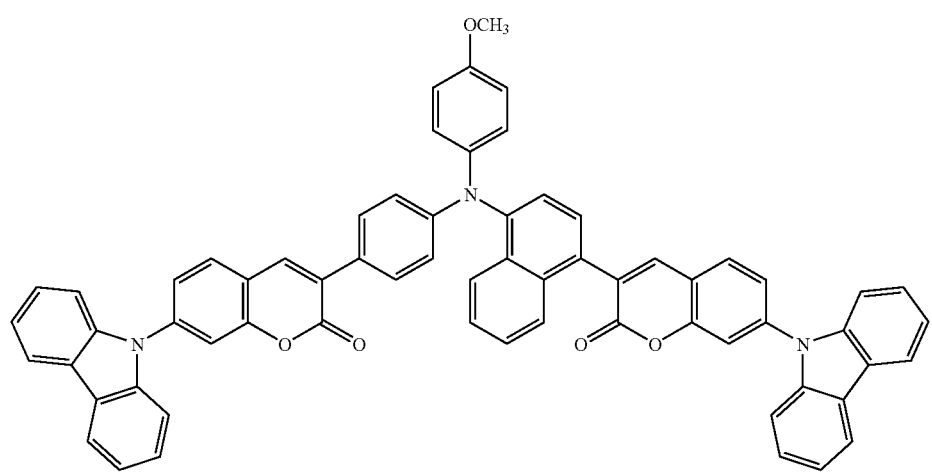
Chemical Formula 14:
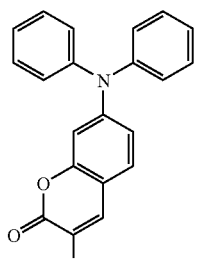

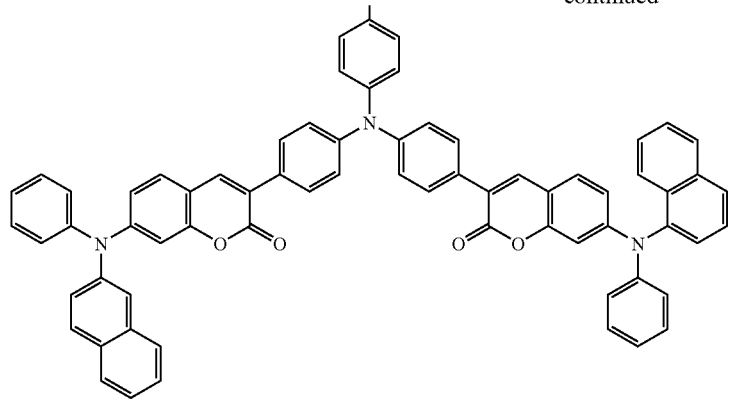
Chemical Formula 15:
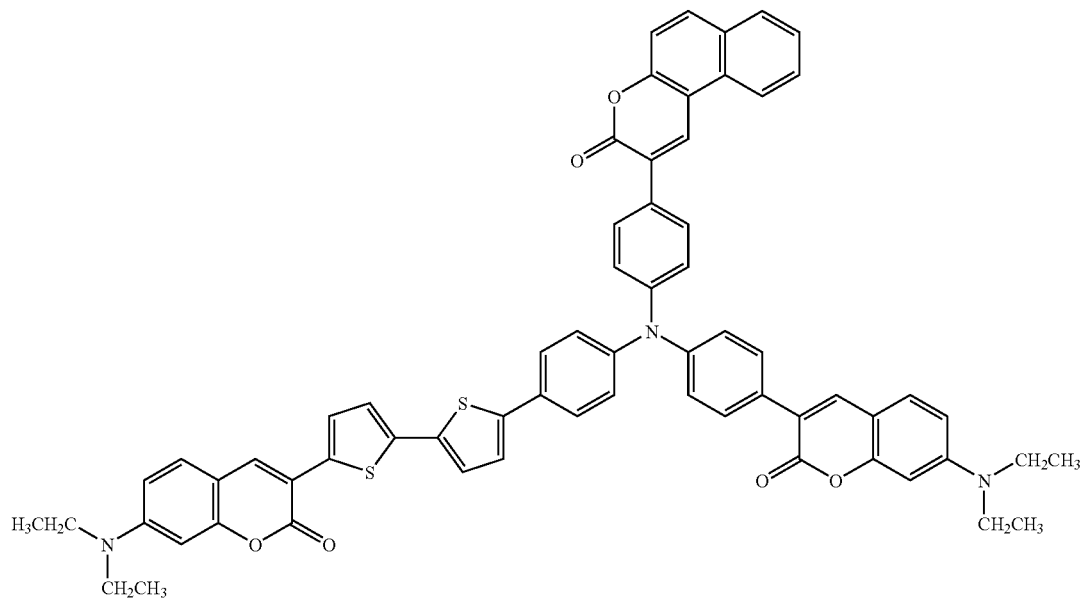
Chemical Formula 16:
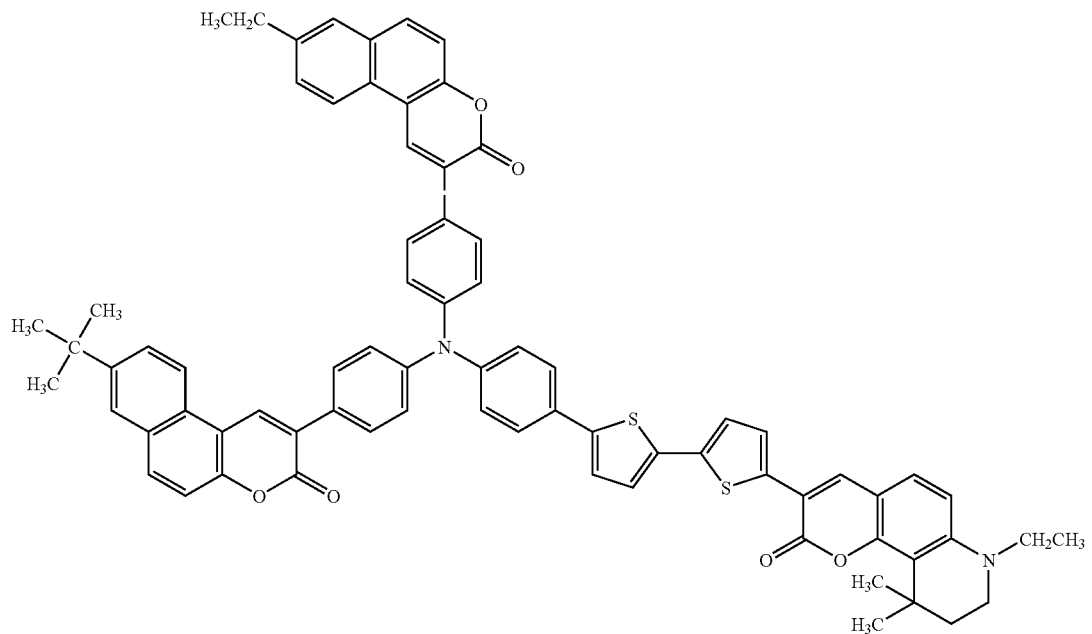

Chemical Formula 17:
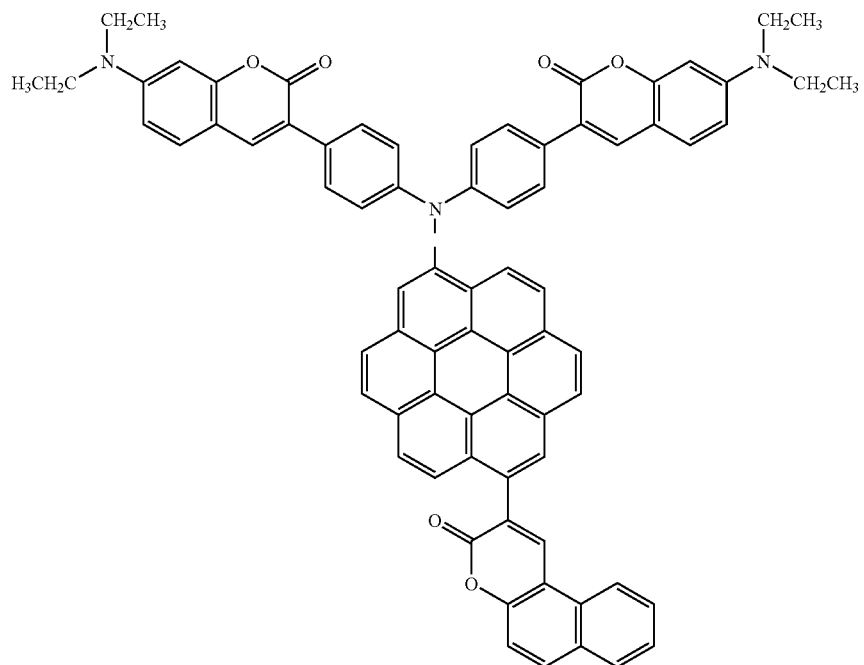
Chemical Formula 18:
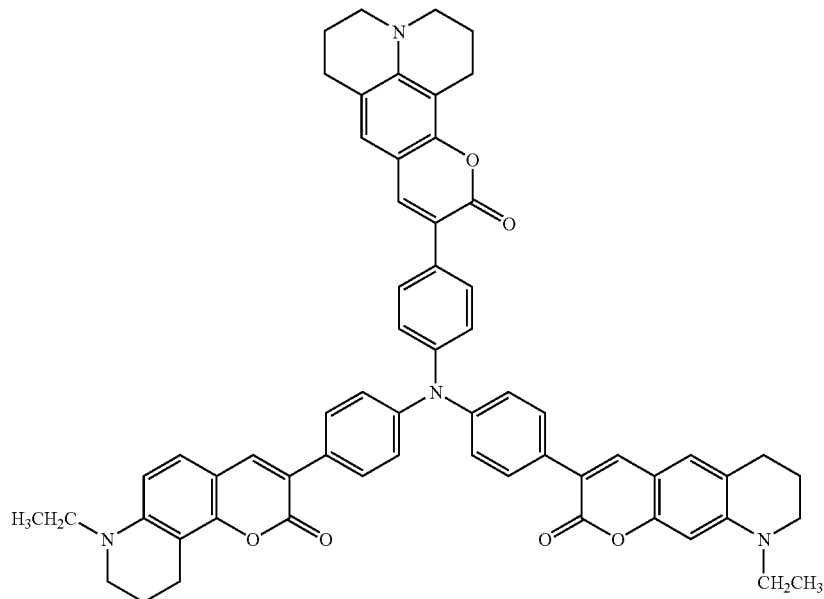
Chemical Formula 19:
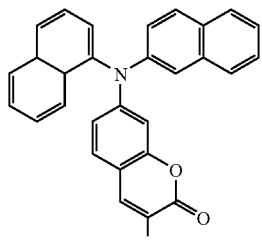

-continued
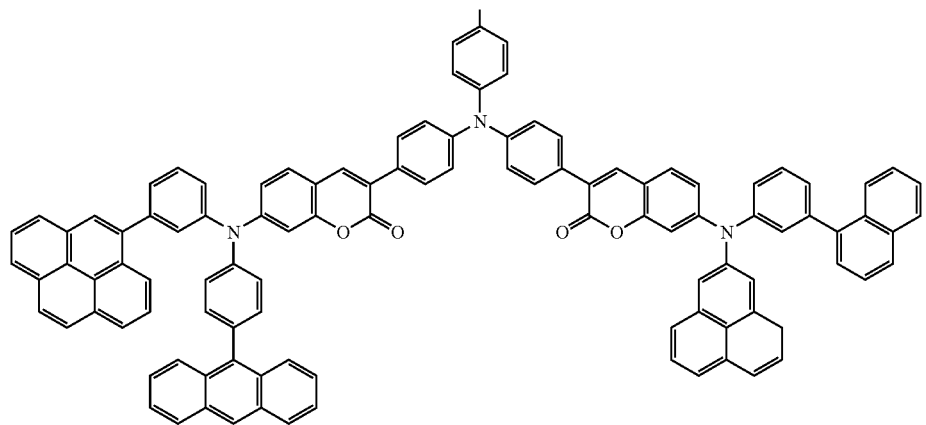
Chemical Formula 20:
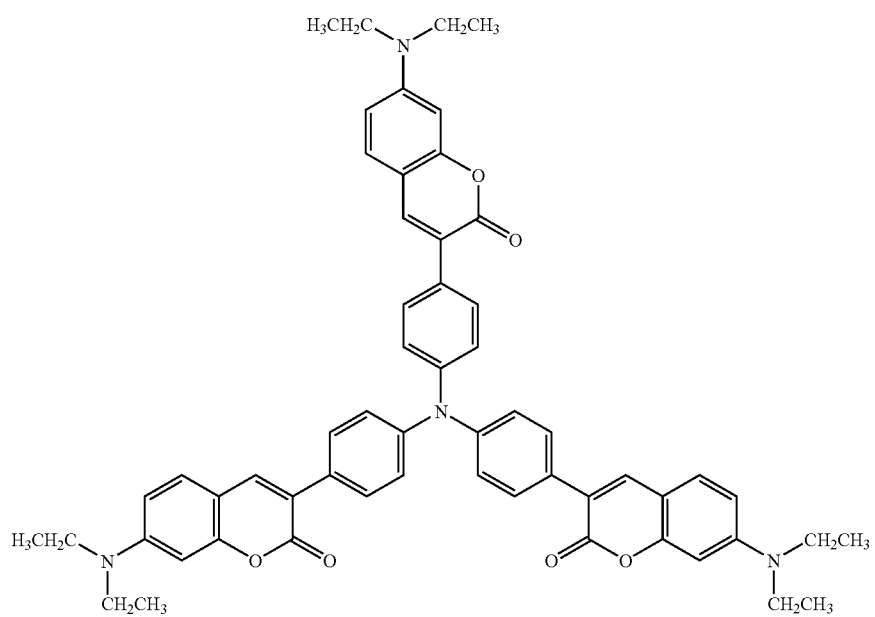
Chemical Formula 21:
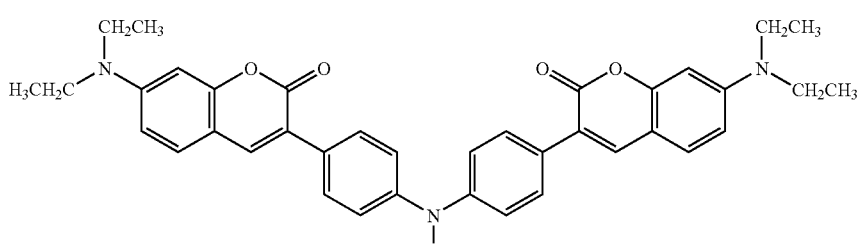

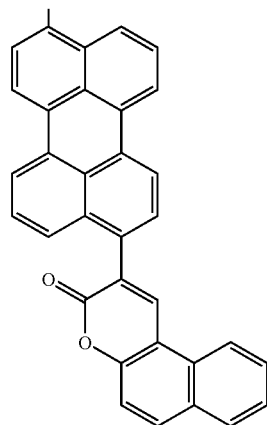
Chemical Formula 22:
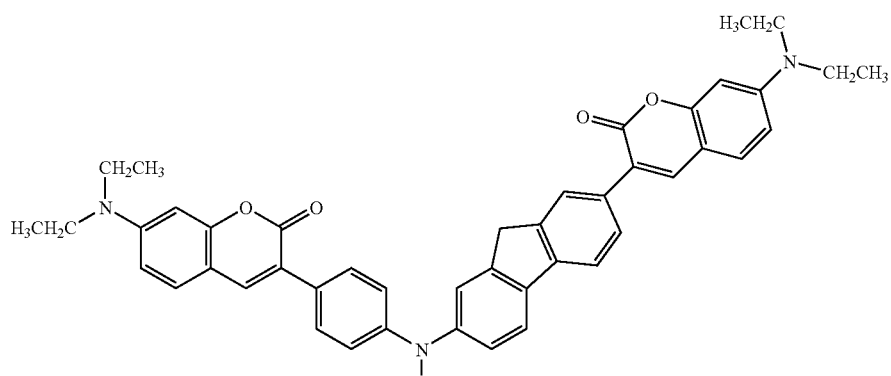
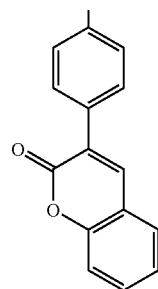
Chemical Formula 23:
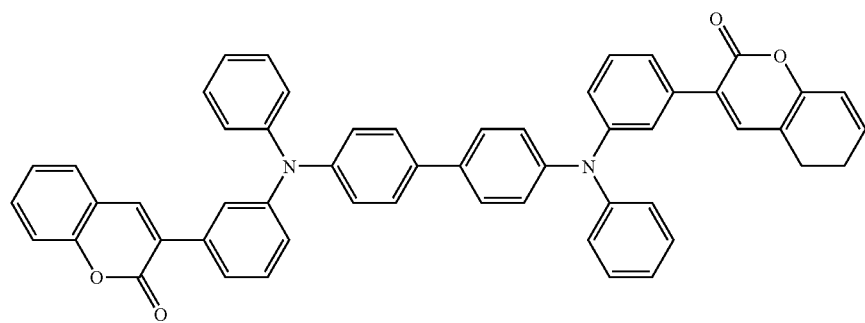

-continued
Chemical Formula 24:
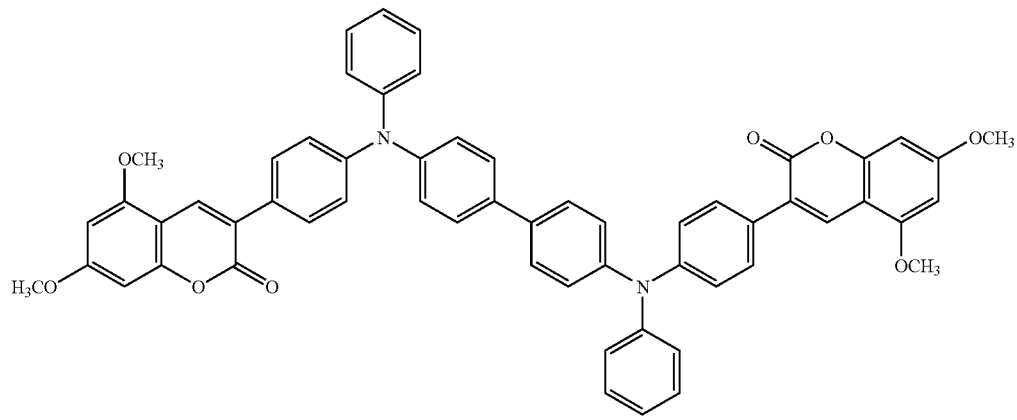
Chemical Formula 25:
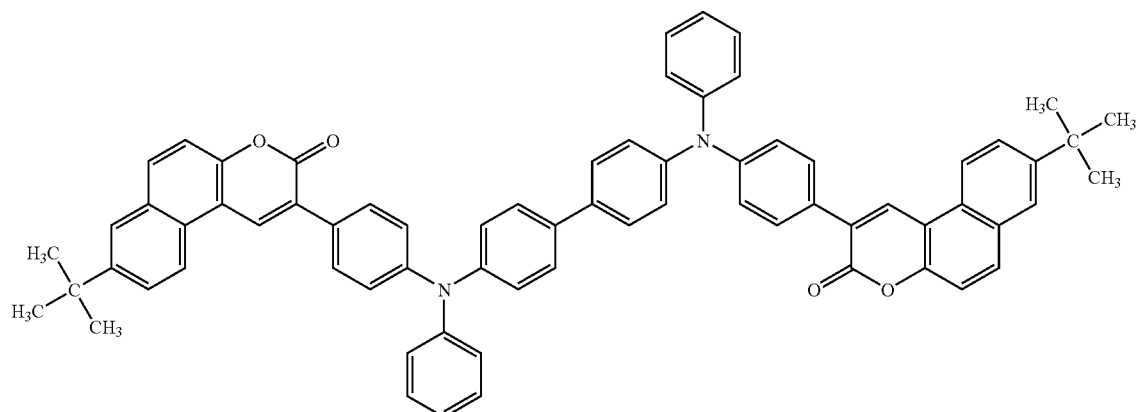
Chemical Formula 26:
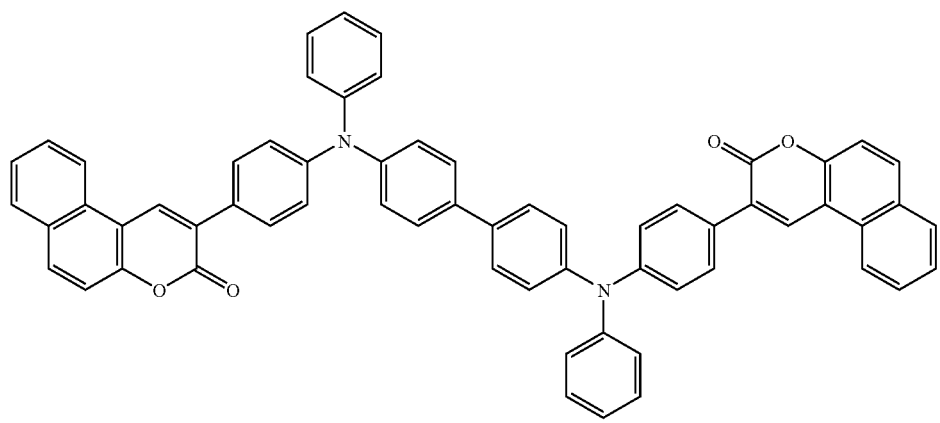

-continued
Chemical Formula 27:
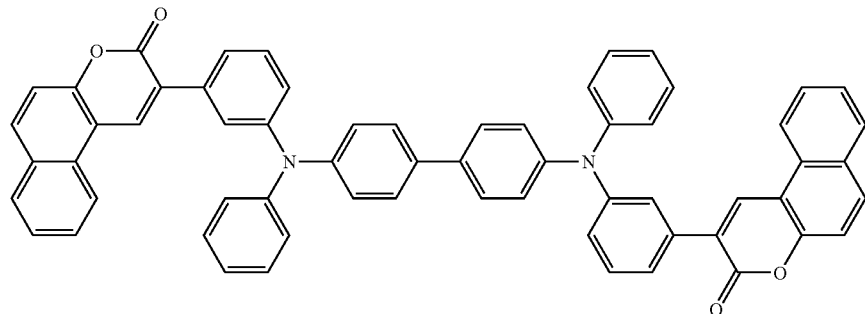
Chemical Formula 28:
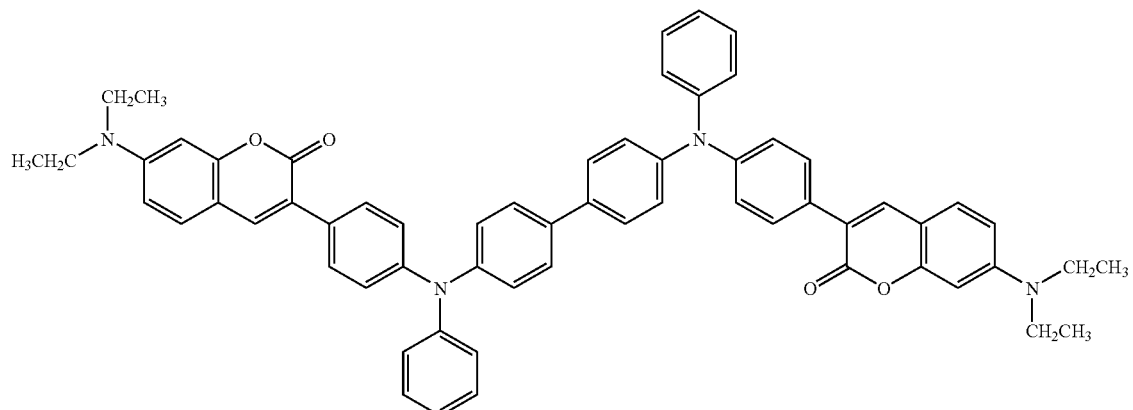
Chemical Formula 29:
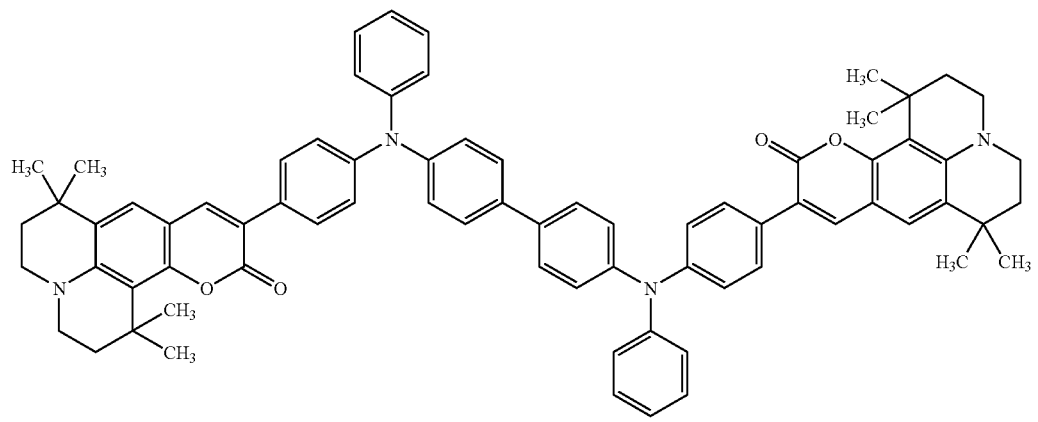
Chemical Formula 30:
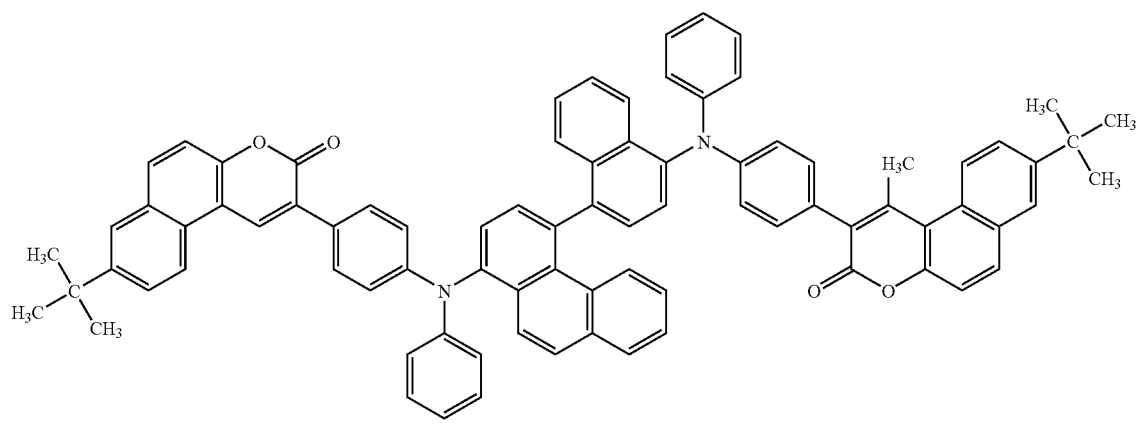

Chemical Formula 31:
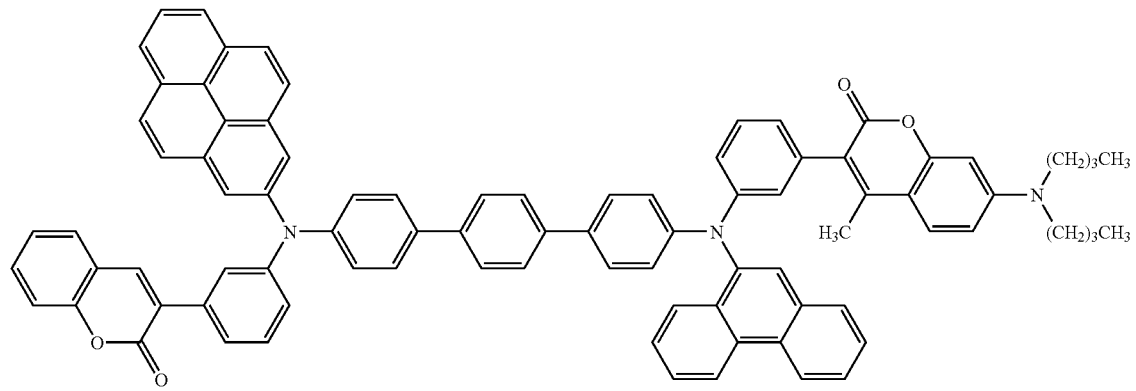
Chemical Formula 32:
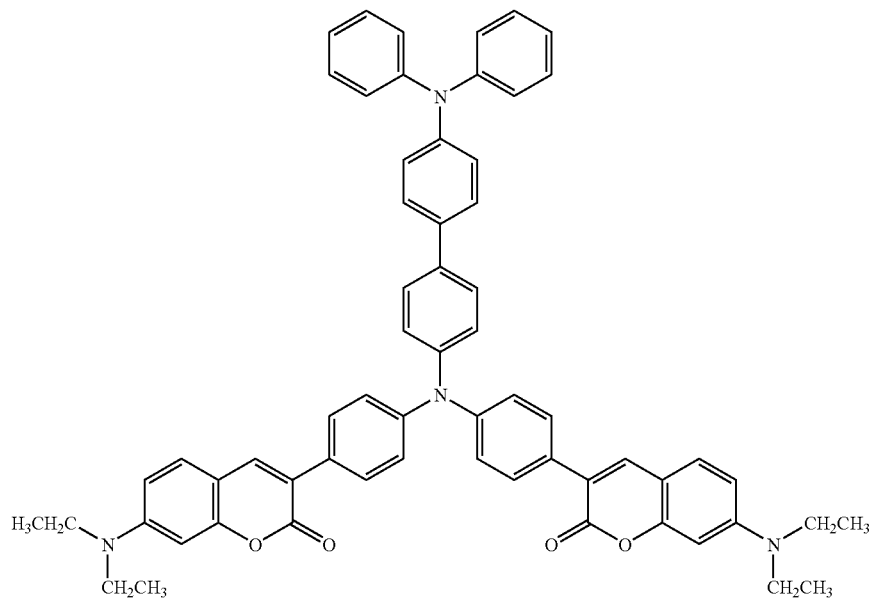
Chemical Formula 33:
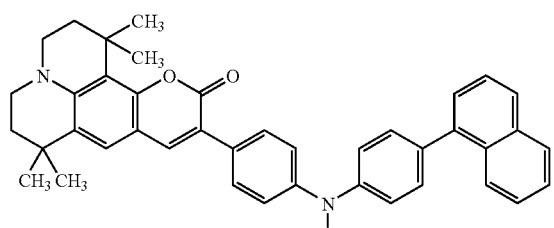

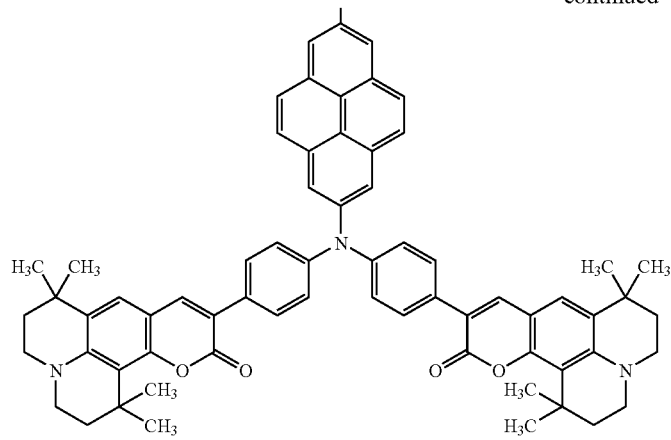
Chemical Formula 34:
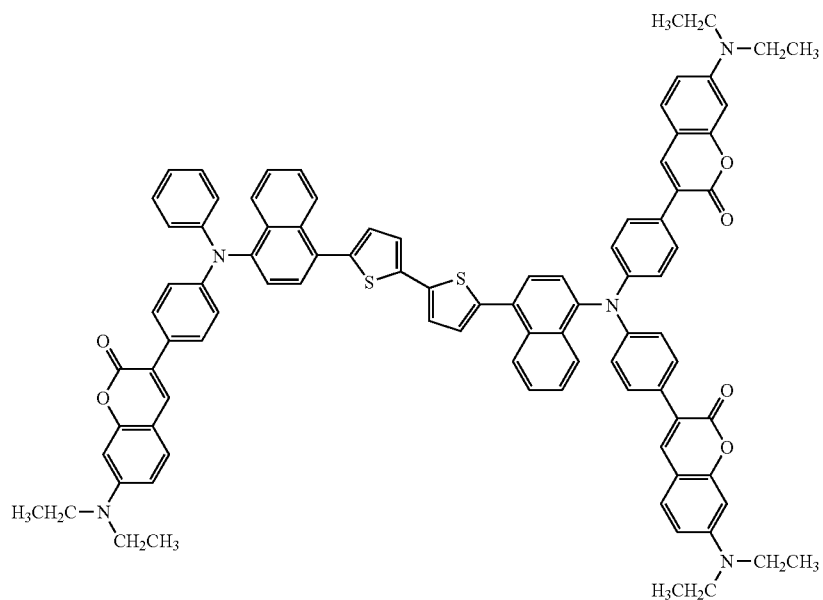
Chemical Formula 35:
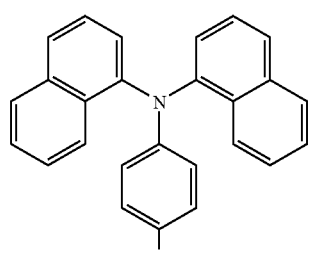

-continued
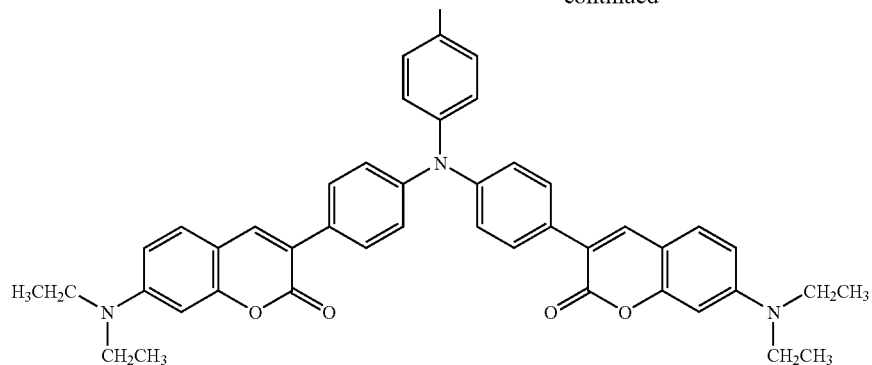
Chemical Formula 36:
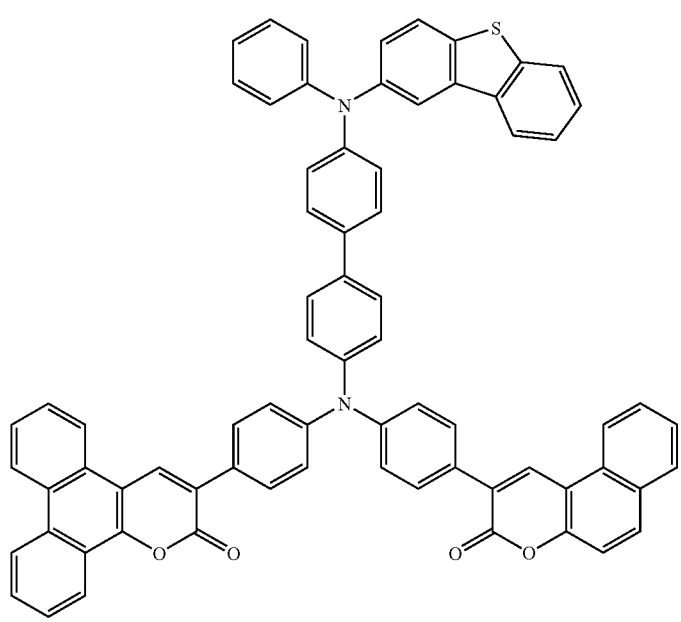
Chemical Formula 37:
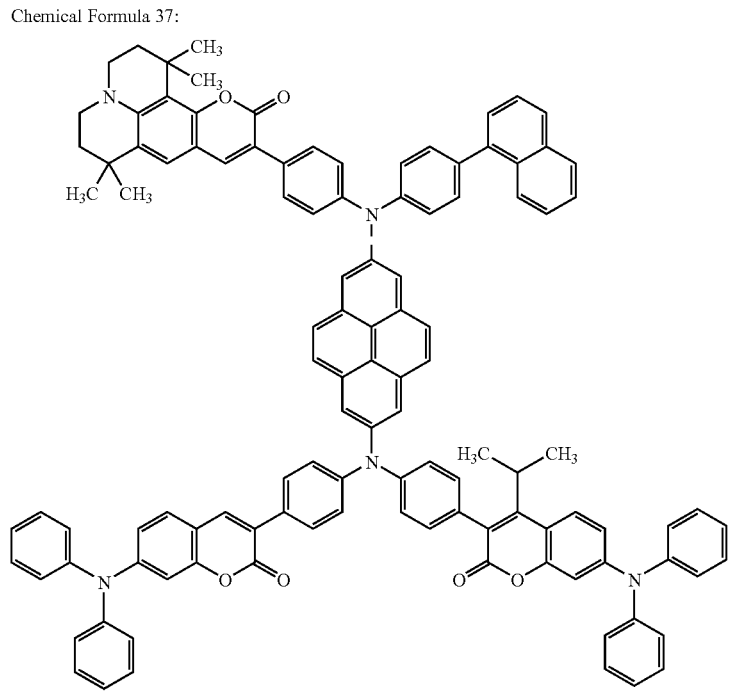

-continued
Chemical Formula 38:
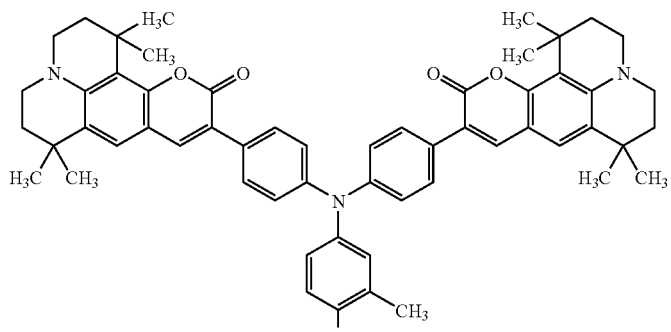
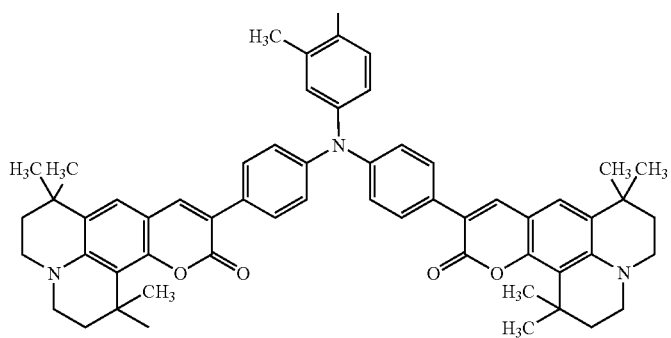
Chemical Formula 39
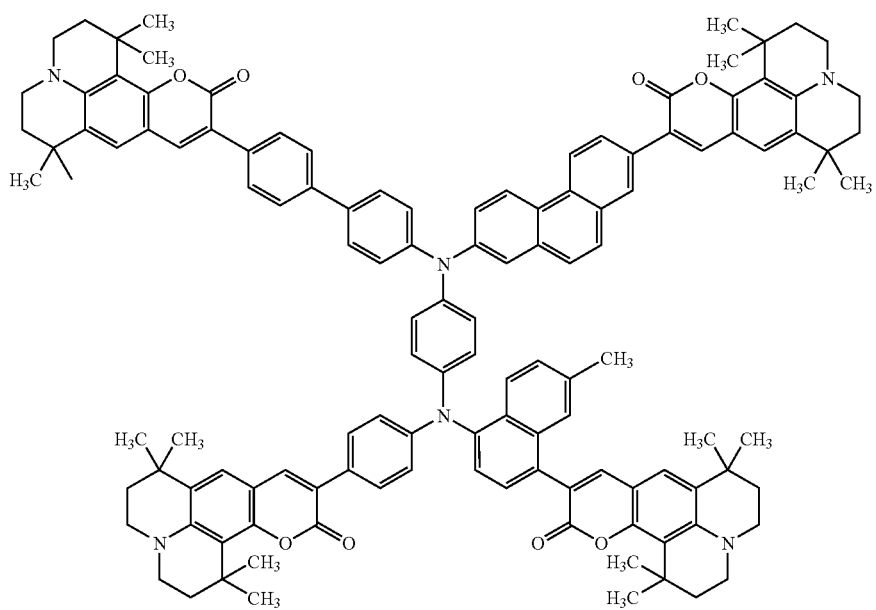

Chemical Formula 40:
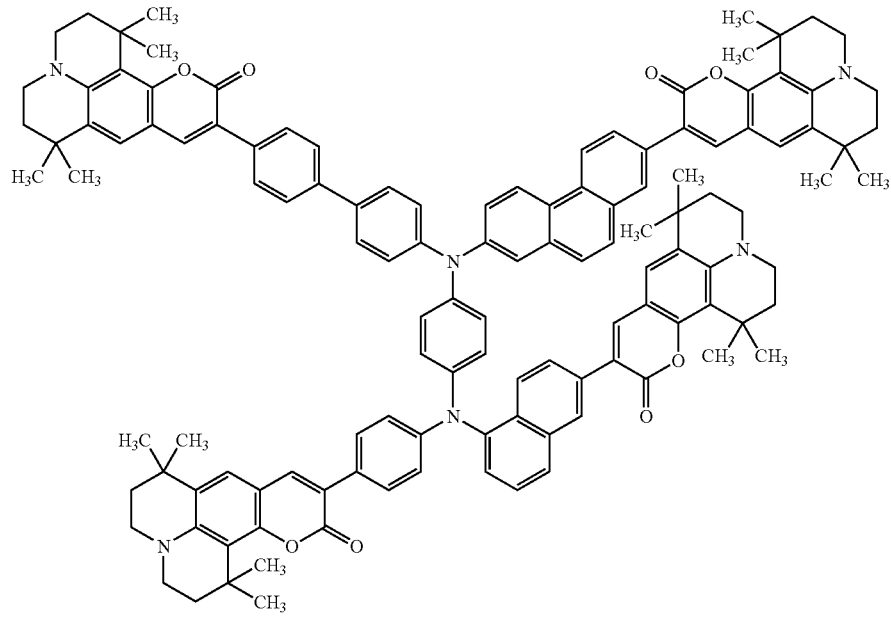
Chemical Formula 41:
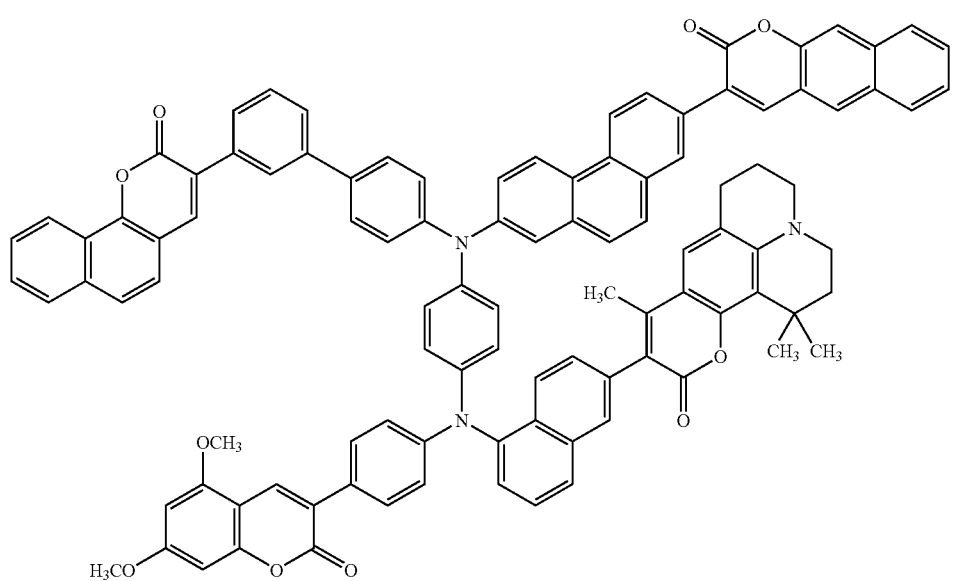

Chemical Formula 42:
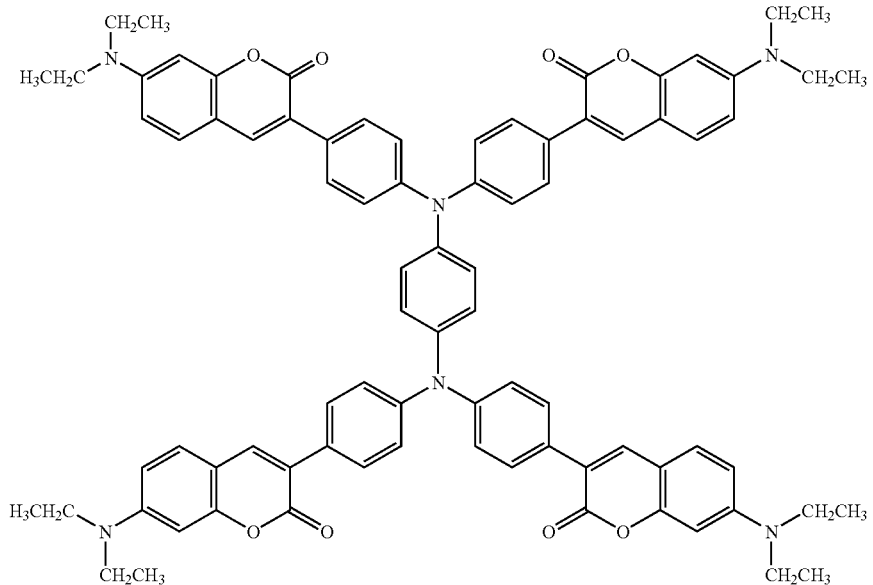
Chemical Formula 43:
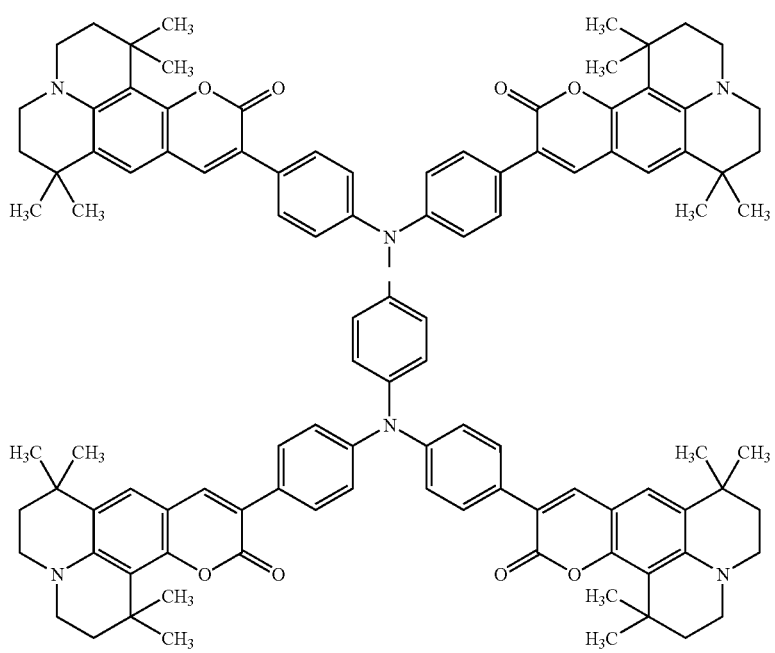
Chemical Formula 44:
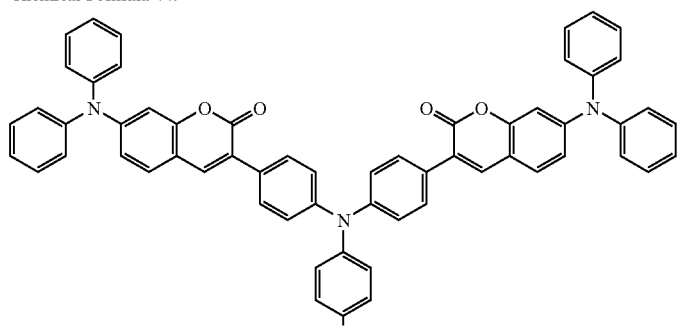

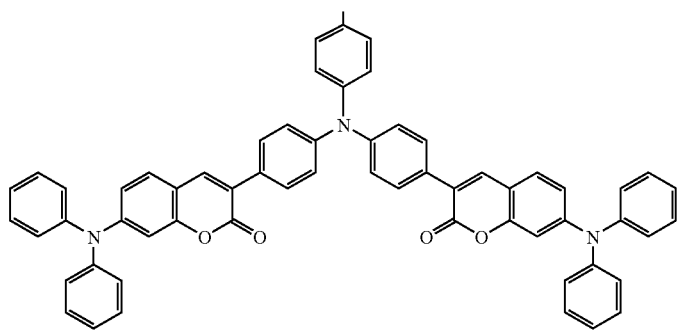
Chemical Formula 45:
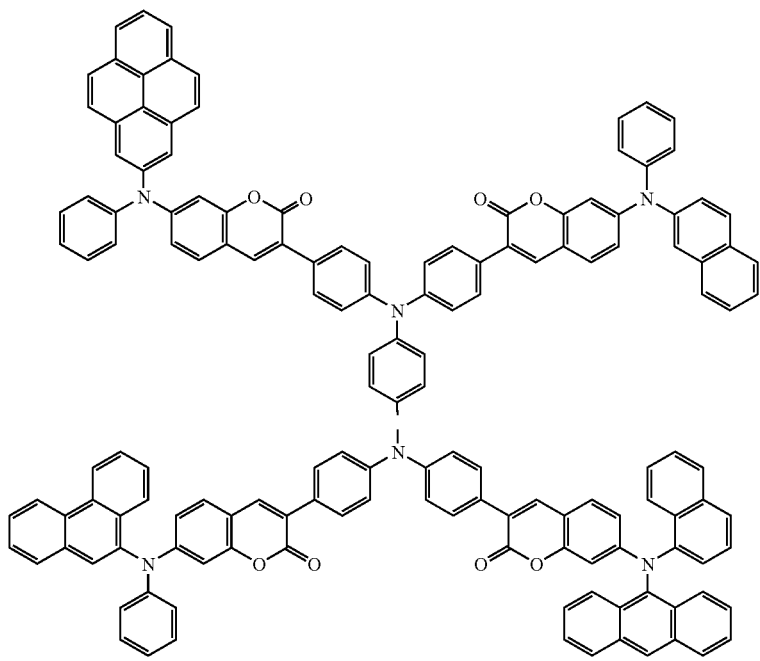
Chemical Formula 46:
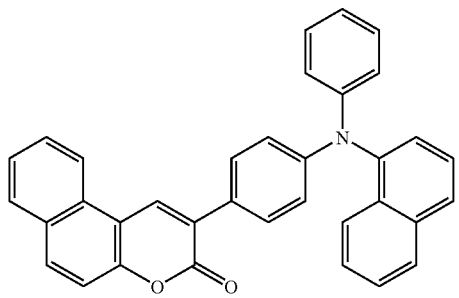
Chemical Formula 47:
Chemical Formula 48:
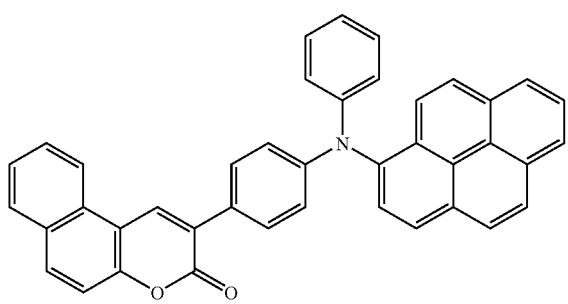

Chemical Formula 49:

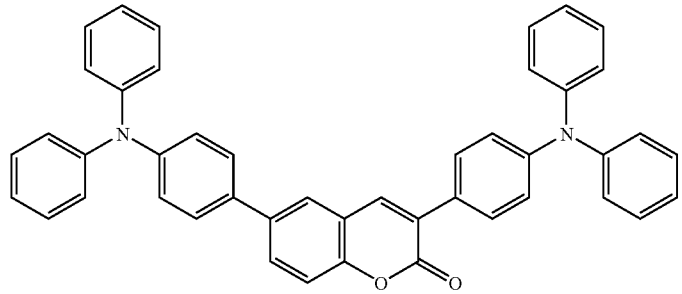

Chemical Formula 50:

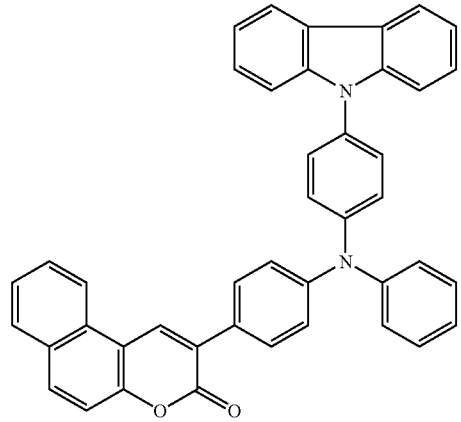

The amine compound of this invention can be prepared in various manners: With an economical viewpoint, it is preferable to employ a process using a nucleophilic substitution reaction between an aromatic halide and an aromatic primary or secondary amine. In case of employing this process, the amine compound of this invention can be produced in a good yield by, for example, allowing a compound represented by General Formula 2, which has $R^1$ to $R^5$ corresponding to those in General Formula 1, to react with a compound which bears within the same molecule an atomic group represented by General Formula 3. X in General Formula 2 denotes a halogen group such as chloro, bromo and iodo groups; and Y in General Formula 3, either of a hydrogen atom, independent phenyl group or benzene ring which shares a part of a condensed polycyclic aromatic hydrocarbon or heterocyclic group.

General Formula 2:

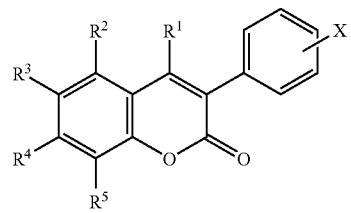

General Formula 3:

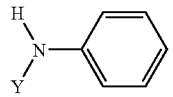

More particularly, adequate amounts of the compounds represented by General Formulae 2 and 3 are placed in a reaction vessel, dissolved in an appropriate solvent, if necessary, admixed with either a metal catalyst, for example, platinum, or an organometallic catalyst such as palladium acetate, potassium tert-butoxide, or tri-tert-butylphosphane, and then allowed to react at ambient or higher temperature while heating and stirring under refluxing conditions.

As to solvents, one can choose hydrocarbons such as pentane, hexane, cyclohexane, octane, benzene, toluene, and xylene; halides such as carbon tetrachloride, chloroform, 1,2-dichloroetane, 1,2-dibromoethane, trichloroethylene, tetrachloroethylene, chlorobenzene, bromobenzene, and α-dichlorobenzene; alcohols and phenols such as methanol, ethanol, 2,2,2-trifluoroethanol, 1-propanol, 2-propanol, 1-butanol, 2-butanol, isobutyl alcohol, isopentyl alcohol, cyclohexanol, ethylene glycol, propylene glycol, 2-methoxyethanol, 2-ethoxyethanol, phenol, benzyl alcohol, cresole, diethylene glycol, triethylene glycol, and glycerin; ethers such as diethyl ether, diisopropyl ether, tetrahydrofuran, tetrahydropyran, 1,4-dioxane, anisole, 1,2-dimethoxyethane, diethylene glycol dimethyl ether, dicyclohexyl-18-crown-6, methylcarbitol, and ethylcarbitol; ketones such as acetone, ethyl methyl ketone, and cyclohexanone; acids and acid derivatives such as acetic acid, acetic anhydride, trichloroacetic acid, trifluoroacetic acid, propionic anhydride, ethyl acetate, butyl acetate, ethylene carbonate, propylene carbonate, formamide, N-methylformamide, N,N-dimethylformamide, N-methylacetoamide, N,N-dimethylacetoamide, hexamethylphosphoric triamide, and trimethyl phosphate; nitriles such as acetonitrile, propionitrile, succinonitrile, and benzonitrile; nitro compounds such as nitromethane and nitrobenzene; sulfur-containing compounds such as dimethylsulfoxide and sulfolane; and water, which may be used in combination, if necessary.

In case of using solvents, generally, a larger amount of solvent leads to a less reaction efficiency, while a less amount of solvent, a more difficulty in homogenous heating and stirring and also a more liability to side reactions. Thus, it is desirable to set the amount of solvent to a level of 100-folds or less, usually, 5 to 50-folds by weight of the total amount of starting compounds to be used. The reaction completes within 10 hours, usually, 0.5 to 5 hours, dependently upon the types of starting compounds and reaction conditions. The progress of reaction can be monitored by conventional method, for example, thin layer chromatography, gas chromatography, and high-performance liquid chromatography. The amine compound of this invention is obtainable in a desired amount by or in accordance with such process. The compounds represented by General Formulae 2 and 3 are obtainable by usual methods for preparing analogous compounds: In case that such a compound is commercially available, one may purify it prior to its use, if necessary.

Depending upon use, the amine compound in a reaction mixture thus obtained may be used intact: However, prior to use, it is usually purified with a method(s) extensively employed in the purification of analogous compounds, such as dissolution, separation, decantation, filtration, extraction, concentration, thin layer chromatography, column chromatography, gas chromatography, high-performance liquid chromatography, distillation, sublimation, and crystallization, which may be applied in combination, if necessary. Depending upon the types of amine compounds and uses of organic EL devices, it is desirable to highly purify the amine compound of this invention to be applied to organic EL devices by means of, for example, distillation, crystallization and/or sublimation, prior to its uses.

Among these, sublimation is superior to others because high-purity crystals can be easily obtained through a single step with a less loss of the amine compound during purification, as well as because solvent is not incorporated in crystals. Although both atmospheric and reduced pressure sublimation methods are applicable in this invention, the latter method is usually employed. To sublimate the amine compound of this invention in vacuo, for example, an adequate amount of the amine compound is placed in a sublimation purification apparatus, and then heated at possible lowest temperature, in particular, at a temperature lower than the melting point while keeping the pressure inside the apparatus at $10^{-2}$ Torr or lower, desirably, $10^{-3}$ Torr or lower so that the amine compound does not decompose. When the purity of an amine compound to be subjected to sublimation purification is lower, the sublimation rate is reduced so as to avoid the incorporation of impurities by increasing or decreasing the pressure and/or the heating temperature in the apparatus, while the sublimation is accelerated by aerating the inner space of the apparatus with an inert gas such as rare gases when the amine compound is less sublimatable. The size of crystals obtained by sublimation can be controlled by elevating or reducing the temperature on the condensation surface in the apparatus: When the condensation surface is kept at a temperature slightly lower than the heating temperature so that the amine compound gradually crystallize, one can obtain crystals in larger sizes.

The following will illustrate the way of using the amine compound of this invention: Since as described heretofore, it has an absorption maximum in the visible region and an elevated molecular absorption coefficient, it would find a variety of applications where it is used as materials to form polymerizable compounds into polymers by exposure to a visible light; to sensitize solar cells; to form a recording layer in optical recording media; to modify the chromaticity of optical filters; and to stain various types of clothes. Particularly, since in many amine compounds according to this invention, their absorption maxima locate near to the oscillation wavelength of conventional visible laser with an oscillation line around 500 nm, particularly, 450 to 550 nm, for example, gas state lasers such as argon ion laser and krypton ion laser, semiconductor lasers such as CdS laser, and solid lasers such as Nd-YAG laser of distributed feedback or Bragg reflection type, they can be very advantageously used as photosensitizer in photopolymerizable compositions to be exposed to a visible laser in the fields of, for example, information storage such as facsimile, copying apparatus, printing apparatus, and holography; printing such as flexography and gravure printing; and printed circuit such as photoresist.

The amine compound of this invention has practical merits that it prevents or reduces troubles and discomforts which may occur in organisms and products when they are exposed to environmental lights such as natural and artificial lights, as well as that it controls the chromaticity, color tone, tint and appearance in products and moderates in products a reflected or transmitted light to give a desired color balance in case that the amine compound of this invention is used, if necessary, in combination with one or more materials capable of absorbing a light in the ultraviolet, visible and/or infrared regions in clothes in general and other products including, for example, building/bedding/decorating products such as drape, lace, casement, print, venetian blind, roller blind, shutter, store curtain, blanket, futon, ticking, quilt cover, bed sheet, cushion, pillow, pillow cover, decorative pillow, mat, carpet, sleeping bag, interior finish for car, window glass and windowpane; sanitary and health goods such as a paper diaper, diaper cover, eyeglasses, monocle, and lorgnette; internal base sheets, linings, and materials for shoes; wrappers; materials for umbrellas; parasols; stuffed toys; filters, panels and screens for lighting devices and information displaying devices which use cathode-ray tubes displays, liquid crystal displays, or plasma displays; sunglasses; sun visors; sunroofs; peeping windows of microwaves and ovens; wrapping materials, injection materials, and vessels for enclosing the above products.

Since the amine compound of this invention has a luminescent maximum such as fluorescent maximum in the visible region and emits a green to red light when excited, it is useful as, for example, laser-active substance in dye lasers which require organic compounds with such properties. In case of using the amine compound of this invention in dye lasers, it is purified and dissolved in an appropriate solvent similarly as in forming conventional dye laser oscillating apparatus, after which the solution is adjusted to the prescribed pH level, if necessary, and then enclosed within a dye cell in the laser oscillating apparatus. The amine compound of this invention is characterized in that it exhibits an amplification gain within a much wider wavelength range in the visible region and a higher resistance to both thermal and light, and a less decay when used for a long period of time in comparison with conventional analogous compounds.

As to additional uses where the light emitting ability of the amine compound according to this invention is feasible, it is useful as luminescent agent to label, for example, enzyme, substrate, antigen, antibodie, soluble receptor, protein, glycolipid and nucleic acid in general to be subjected to qualitative and quantitative analyses which utilize specific reactions between distinct substances derived from living bodies, such as enzymatic reaction, antigen-antibody reaction, intra- or extra-cellular signal transmission, formation of protein complexes, and hybridization of nucleic acids with other nucleic acids or proteins. Biosubstances labeled with the amine compound of this invention are very useful in the fields of research and diagnose.

By the way, the amine compound according to this invention is very useful as luminescent agent alone or in combination with other luminescent compounds in organic EL devices which emit a visible light in the green to red region because, as mentioned above, it has a luminescent maximum such as fluorescent maximum at a wavelength around 500 to 650 nm that allows it to emit a visible light in the green to red region when excited, and forms a stable thin membrane when in a glass state, as well as because the amine compound is usually high in thermal resistance. The term "organic EL device" as referred to as in this invention means electroluminescent devices in general which use such amine compound: One of the most important targets to which this invention is applied is an organic EL device of mono- and multi-layer type comprising a cathode to be energized with a positive voltage, an anode to be energized with a negative voltage, a luminescent layer where holes and electrons are allowed to recouple each other so as to give luminescence, and arbitrarily a hole injection/transportation layer for injecting and transporting holes from the anode, an electron injection/transportation layer for injecting and transporting electrons from the cathode, and a hole-blocking layer for suppressing the transportation of holes from the luminescent layer to the electron injection/transportation layer.

As well known in the art, the basic operation of organic EL devices essentially consists of the steps of injecting electrons and holes from electrodes, allowing the electrons and holes to move in solids, allowing the electrons and holes to recouple each other to give singlet or triplet excitons, and allowing the excitons to emit a light: These steps are essentially involved in organic EL devices, regardless of mono- or multi-layer type. However, in organic EL devices of mono-layer type, the characteristics in the above described four steps can be improved only by modifying or altering the molecular structures of luminescent compounds, while in multi-layer type of organic EL devices, the functions to be required for each step can be distributed to a plurality of materials so that they can be independently optimized: Thus, a prescribed performance is usually attainable with a more ease by forming devices into multi-layer type in comparison with case of forming them into mono-layer type.

Because of these, the organic EL device of this invention will be explained hereinafter with reference to an example for multi-layered organic EL device: FIG. 1 is a brief figure of an example for multi-layered organic EL device according to this invention. In FIG. 1, the reference numeral 1 represents a substrate which is provided by forming a substrate material including glass such as aluminosilicate glass, aluminoborosilicate glass, silica glass, soda lime glass, barium silicate glass, barium borosilicate glass or borosilicate glass; or a plastic such as aramid, polyacrylate, polyallylate, polyimide, polyurethane, polyetherketone, polyethersulfone, polyester, polyethylene, poly(ethylene terephthalate), polyolefin, polycarbonate, polysulfone, poly(vinyl chloride), polypropylene, poly(methyl acrylate), epoxy resin, phenol resin, fluorine resin or melamine resin; or a ceramic such as alumina, silicon, quartz or silicon carbide into a plate, sheet or film which may be laminated each other, if necessary. Among these, preferred substrate materials are a glass for photomask such as aluminosilicate glass, aluminoborosilicate glass, quartz glass, borosilicate glass, and barium borosilicate glass which are low in both alkali content and thermal expansion coefficient, plane and free of scratch on their surface and easily grindable; and plastics such as aramids, epoxy resins, phenol resins, polyallylates, polyimides, polyesters, aromatic polyethers, polyolefins, melamine resins, and fluorine resins which are superior in affinity to their adjacent electric conductive membranes and less in moisture permeability, while opaque ceramic materials such as silicon may be used in combination with transparent electrode materials.

The reference numeral 2 in FIG. 1 represents an anode, which is formed by preparing one or more metals or electric conductive compounds low in electric resistivity but high in optical transmissivity throughout the visible region into a single or plurality of membranes with a thickness of 10 to 1,000 nm, desirably, 50 to 500 nm to give an electric resistivity of 1 kΩ/□ or lower, desirably, 5 to 50 Ω/□ for the anode 2 with a method such as vacuum deposition, spattering, chemical vapor deposition (CVD), atom layer epitaxy (ALE), embrocation or immersion while allowing the membrane(s) to contact with either surface of the substrate 1. Examples of electric conductive materials feasible in the anode 2 are metals such as gold, platinum, aluminium and nickel; metal oxides such as zinc oxide, tin oxide, indium oxide and mixtures of tin oxide and indium oxide (abbreviated as "ITO" hereinafter); and electric conductive oligomers and polymers of repeating aniline, thiophene or pyrrole units. Among these, ITO is characterized in that one can easily obtain a preparation with a reduced resistivity, as well as in that minute patterns can be easily provided by etching with acids.

The reference numeral 3 in FIG. 1 represents a hole injection/transportation layer, which is usually formed with a method similar to that used in the anode 2 by preparing the hole injection/transportation layer material into a membrane with a thickness of 1 to 1,000 nm while allowing it to contact with the anode 2. As to hole injection/transportation layer materials, it is desirable to choose a material which exhibits a low ionization potential and a hole mobility of, for example, at least $10^{-6}$ cm$^2$/V·second under an electric field of $10^4$ to $10^6$ V/cm so as to facilitate the injection and transportation of holes from the anode 2. Particular hole injection/transportation layer materials are, for example, arylamine, imidazole, oxadiazole, oxazole, triazole, chalcone, styryl anthracene, stilbene, tetraarylethene, triarylamine, triarylethene, triarylmethane, phthalocyanine, fluorenone, hydrazone, N-vinylcarbazole, pyrazoline, pyrazolone, phenylanthracene, phenylenediamine, polyarylalkane, polysilane, polyphenylenevinylene, and porphyrin derivatives, which are usually used in organic EL devices: These may be used in combination, if necessary. Among these, the much more preferable are monomers and polymers in an aromatic tertiary amine form, which are of arylamines such as monoarylamine, diarylamine, triarylamine and tetraarylamine.

The reference numeral 4 in FIG. 1 represents a luminescent layer, which is usually formed with a method similar to that used in the anode 2 by preparing one or more amine compounds of this invention alone or in combination with one or more appropriate host or guest compounds into a membrane with a thickness of 1 to 1,000 nm, preferably, 10 to 200 nm while allowing it to contact with the hole injection/transportation layer 3. Unlike conventional luminescent layer materials having a coumarin skeleton, the amine compound of this invention forms a luminescent layer in organic EL devices when used alone or in combination with one or more host or guest compounds because it readily forms excitons such as singlet or triplet excitons, as well as giving a desirable energy level for luminescences such as fluorescence and phosphorescence. Particularly, when the amine compound of this invention as host compound is used with an appropriate guest compound, one can obtain a luminescent brightness, electric power efficiency, external quantum efficiency, and life expectancy in extremely high levels which are never attainable with an ease by using conventional host compound. When the amine compound of this invention is used as guest compound, the luminescent brightness in a device can be enhanced by increasing a mixture ratio of the amine compound against a host compound in the luminescent layer because it is less liable to "concentration quenching" for luminescence due to luminescent layer materials. In an organic EL device according to this invention where its luminescent layer is formed by combination of host and guest compounds, the guest compound to be used is equimolar or less to the host compound, usually, 0.1 to 10 mol %, desirably, 0.5 to 5 mol % to the host compound: Both compounds are formed into a single membrane or adjacent separate membranes with a thickness of 1 to 1,000 nm, preferably, 10 to 200 nm, thus preparing the luminescent layer 4.

In case of using the amine compound of this invention as host, additional host compounds to be used in combination therewith are, for example, quinolinol metal complexes, condensed polycyclic aromatic hydrocarbons, for example, anthracene, chrysene, coronene, triphenylene, naphthacene, naphthalene, phenantlene, picene, pyrene, fluolene, perylene, benzopylene, and their derivatives; hydrocarbon ring assemblies such as quaterphenyl, distylylarylene, 1,4-diphenylbutadiene, stilbene, terphenyl, tetraphenylbutadiene, biphenyl, and their derivatives; heterocyclic compounds such as oxadiazole, carbazole, pyridazine, benzimidazole, benzoxazole, benzothiazole, and their derivatives; quinacridone, rubrene compounds, and their derivatives; polymethyne dyes of stylyl type; and adamantane derivatives, which are usually used in organic EL devices.

Among these host compounds, the much more preferable are, for example, quinolinol metal complexes. The term "quinolinol metal complex" as referred to as in this invention means complexes in general comprising a quinolinol, such as 8-quinolinol and benzoquinoline-10-ol, which bears within the same molecule a pyridine residue and a hydroxyl group and behaves as ligand; and a univalent, divalent or trivalent metal or its oxide of the group 1, 2, 12, or 13 in the periodic table, such as lithium, sodium, potassium, beryllium, magnesium, calcium, zinc, boron, aluminum, gallium, and indium, which behaves as center metal and receives an electron pair from the nitrogen atom in the pyridine residue to form a coordinate bond with the ligand. In case that the ligand is either 8-quinolinol or benzoquinoline-10-ol, it may bear one or more substituents, never hindering carbon(s) other than those at the 8- or 10-position, to which hydroxyl group(s) is linked, from bearing one or more substituents, for example, halogen groups such as fluoro, chloro, bromo, and iodo groups; aliphatic hydrocarbon groups such as methyl, ethyl, propyl, isopropyl, butyl, isobutyl, sec-butyl, tert-butyl, pentyl, isopentyl, neopentyl, and tert-pentyl groups; ether groups such as methoxy, ethoxy, propoxy, isopropoxy, butoxy, isobutoxy, sec-butoxy, tert-butoxy, pentyloxy, isopentyloxy, hexyloxy, phenoxy, and benzyloxy groups; ester groups such as acetoxy, benzoyloxy, methoxycarbonyl, ethoxycarbonyl, and propoxycarbonyl groups; cyano group; nitro group; sulfo group; and combinations thereof. In case that a quinolinol metal complex has two or more ligands within the same molecule, they may be the same or different each other.

Particular quinolinol metal complexes are, for example, aluminium complexes such as aluminium-tris(8-quinolinolato), aluminium-tris(3,4-dimethyl-8-quinolinolato), aluminium-tris-(4-methyl-8-quinolinolato), aluminium-tris(4-methoxy-8-quinolinolato), aluminium-tris(4,5-dimethyl-8-quinolinolato), aluminium-tris-(4,6-dimethyl-8-quinolinolato), aluminium-tris(5-chloro-8-quinolinolato), aluminium-tris(5-bromo-8-quinolinolato), aluminium-tris-(5,7-dichloro-8-quinolinolato), aluminium-tris(5-cyano-8-quinolinolato), aluminium-tris(5-sulfonyl-8-quinolinolato), aluminium-tris-(5-propyl-8-quinolinolato), and aluminium-oxide-bis(2-methyl-8-quinolinolato); zinc complexes such as zinc-bis(8-quinolinolato), zinc-bis(2-methyl-8-quinolinolato), zinc-bis(2,4-dimethyl-8-quinolinolato), zinc-bis(2-methyl-5-chloro-8-quinolinolato), zinc-bis(2-methyl-5-cyano-8-quinolinolato), zinc-bis(3,4-dimethyl-8-quinolinolato), zinc-bis(4,6-dimethyl-8-quinolinolato), zinc-bis(5-chloro-8-quinolinolato), and zinc-bis(5,7-dichloro-8-quinolinolato); beryllium complexes such as beryllium-bis(8-quinolinolato), beryllium-bis(2-methyl-8-quinolinolato), beryllium-bis(2,4-dimethyl-8-quinolinolato), beryllium-bis(2-methyl-5-chloro-8-quinolinolato), beryllium-bis(2-methyl-5-cyano-8-quinolinolato), beryllium-bis(3,4-dimethyl-8-quinolinolato), beryllium-bis(4,6-dimethyl-8-quinolinolato), beryllium-bis(5-chloro-8-quinolinolato), beryllium-bis(4,6-dimethyl-8-quinolinolato), and beryllium-bis(10-hydroxybenzo[h]quinolinolato); magnesium complexes such as magnesium-bis(8-quinolinolato), magnesium-bis(2-methyl-8-quinolinolato), magnesium-bis(2,4-dimethyl-8-quinolinolato), magnesium-bis(2-methyl-5-chloro-8-quinolinolate), magnesium-bis(2-methyl-5-cyano-8-quinolinolato), magnesium-bis(3,4-dimethyl-8-quinolinolato), magnesium-bis(4,6-dimethyl-8-quinolinolato), magnesium-bis(5-chloro-8-quinolinolato), and magnesium-bis(5,7-dichloro-8-quinolinolato); indium complexes such as indium-tris(8-quinolinolato); gallium complexes such as gallium-tris(5-chloro-8-quinolinolato); and calcium complexes such as calcium-bis(5-chloro-8-quinolinolato), which may be used in combination, if necessary.

Examples of such a guest compound to be used in this invention are oxazone derivatives such as acridone derivatives and Nail-Red; quinuclidone derivatives; coumarin derivatives disclosed in Japanese Patent Kokai Nos. 2001-76875, 2001-76876, 2001-329257, 2002-226484, 2003-249371, 2003-249372, and 2004-6222; cinnamate derivatives; diketopyrrolopyrrole derivatives; stilbene derivatives such as 1,1,4,4-tetraphenyl-1,3-butadiene, 4,4'-bis(2,2-diphenylvinyl)biphenyl, and 4,4'-bis [(1,1,2-triphenyl)ethenyl]biphenyl; polycyclic aromatic compounds such as anthracene, 9,10-diphenylanthracene, 9,10-bis(phenylethyl)anthracene, chrysene, coronene, decacyclene, tetracene, tetraphenylcyclopentadiene, 4,4-bis(9''-ethynylanthracenyl)biphenyl, pyrene, perylene, dibenzo [ff]diindeno[1,2,3-cd:1',2',3'-lm]perylene, 1,4-bis(9'-ethynylanthracenyl)benzene, pentaphenylcyclopentadiene, and rubrene and their derivatives; triarylamine compounds; pyrazine derivatives; pyran derivatives such as 4-(dicyanomethylene)-2-tert-butyl-6-(1,1,7,7-tetramethyljulolidyl-9-enyl)-4H-pyrane; benzoimidazole derivatives; benzoxazole derivatives; benzothiazole derivatives; polyterphenylenevinylene and its derivatives; polythienylenevinylene and its derivatives; polythiophene and its derivatives; polynaphthylenevinylene and its derivatives; poly-N-vinylcarbazole and its derivatives; polyphenylenevinylene and its derivatives; and polyfluorene and its derivatives, which are usually used in this art: These may be used in combination, if necessary. As described heretofore, the amine compound of this invention effectively functions as not only host but also guest in organic EL devices. In case of using the amine compound of this invention as guest compound, it is arbitrary combined with other guest compound chosen from those described in the above, thus forming the luminescent layer in organic EL devices.

The reference numeral 5 in FIG. 1 represents an electron injection/transportation layer, which is usually formed with a method similarly as in the anode 2 by preparing one or more organic compounds high in electron affinity or, for example, anthraquinodimethane, anthrone, oxaziazole derivatives, carbodiimide, distyrylpyrazine, diphenylquinone, silazane, thiopyrandioxide, triazole, tetracarboxylate of heterocyclic compound, phthalocyanine, fluorenone derivatives, quinolinol metal complexes similar to those in the luminescent layer 4, or a conductive oligomer or polymer of repeating aniline, thiophene, or pyrrole units into a membrane with a thickness of 10 to 500 nm while allowing it to contact with the luminescent layer 4. In case that a plurality of electron injection/transportation layer materials are used, they may be mixed to homogeneity and then formed into a single layer, and alternatively formed into a plurality of separate layers without premixing while allowing each layer to contact with its adjacent layer(s) In case of providing a hole-blocking layer, a hole-blocking layer material, for example, an oxadiazole compound such as 2-biphenyl-4-yl-5-(4-tert-butylphenyl)-☐1,3,4☐oxadiazole, 2,2-bis☐-(4-biphenyl)-1,3,4oxadiazole-2-yl-1,4-phenylene☐hexafluoropropane, and 1,3,5-tris-(2-naphthalene-1-yl-☐1,3,4☐oxadiazole-5-yl)benzen is prepared into a membrane with a method similar to that used in the anode 2 while allowing it to contact with the luminescent layer 4, prior to the formation of the electron injection/ transportation layer 5. The thickness of such a hole-blocking layer is set to a level in the range of 1 to 100 nm, usually, 5 to 50 nm while considering the thickness of the electron injection/transportation layer 5 and the operation characteristics of organic EL devices.

The reference numeral 6 in FIG. 1 represents a cathode, which is usually formed by depositing one or combination of metals such as lithium, magnesium, calcium, sodium, potassium, silver, copper, aluminium, indium, ytterbium, their alloys or metal oxides, or electric conductive compounds with a work function (usually not higher than 5 eV) lower than that for the compound to be used in the electron injection/transportation layer 5 while allowing the resultant layer to come into contact with the electron injection/transportation layer 5. There is provided no limitation for the thickness of the cathode 6: It is set to 10 nm or more in thickness, desirably, 50 to 500 nm to give a resistivity of 1 k$\Omega$/□ or lower while considering electric conductivity, production cost, thickness of device, and optical transmittance. There may be provided an interfacial layer of aromatic diamine, quinaqcridone, naphthacene, organosilicon or organophosphorus compounds between the cathode 6 and electron injection/transportation layer 5 containing the organic compounds in order to improve their cohesiveness, if necessary. Furthermore, to facilitate the transportation of electrons from the cathode 6 to the injection/transportation layer 5, there may be provided with a method similar to that used in the anode 2 a thin membrane of alkaline metal or alkaline earth metal compound such as lithium fluoride or lithium oxide, 0.1 to 2 nm in thickness, on the side to be contacted with the electron injection/transportation layer 5 in the cathode 6.

As explained heretofore, the organic EL device of this invention can be obtained by providing in one device an anode, luminescent layer, cathode, and arbitrarily a hole injection/transportation layer, electron injection/transportation layer, and/or hole-blocking layer on the same substrate while allowing each layer to contact with their adjacent layer(s). During the formation of each layer, it is desirable to carry out all the working steps under high vacuum conditions, particularly, at a pressure of $10^{-5}$ Torr or lower to minimize the oxidation and decomposition of organic compounds, as well as to minimize the adsorption of oxygen and water. In the formation of a luminescent layer, the ratio of host and guest compounds can be adjusted by premixing them in a pre-scribed ratio, and alternatively by separately controlling the heating velocities for respective compounds in vacuum sublimation. To minimize deterioration under operation conditions, it is desirable either to seal a part or the whole of the organic EL device thus obtained with a sealing glass or metallic cap in the stream of an inert gas, or to coat or cover it with a moisture-proof paint or protecting layer such as those of ultraviolet-setting resins. Depending upon the structures of organic EL devices, in order to allow the luminescent layer to release a luminescence outside the device with an improved efficiency, one can employ one or combination of diffracting means which change the incident angle of the luminescence with respect to the luminescence-releasing plane in the device, for example, bracelet plates and reflection or transmission gratings in one- or two-dimensional type to suppress the total reflection at the interface between the organic and inorganic layers in the devices and/or the luminescence-releasing plane and the air.

The following will illustrate the way of using the organic EL device of this invention: It is driven by intermittently energizing it with a relatively high pulse voltage, or continuously energizing it with a relatively low non-pulse voltage, usually, 2 to 50 V, depending upon its uses. The organic EL device of this invention gives a luminescence only when anode potential exceeds cathode potential. Thus, both dc or ac voltages are feasible to energize the organic EL device of this invention, and the waveform and frequency of such a voltage is arbitrarily chosen. When energized with ac, the organic EL device of this invention increases and decreases the brightness of luminescence, and repeat on/off for luminescence due to its principle, dependently upon the waveform and frequency of ac to be energized. In the case of the organic EL device in FIG. 1, when a voltage is energized between the anode 2 and cathode 6, holes injected from the anode 2 move into the luminescent layer 4 through the hole injection/transformation layer 3, and electrons injected from the cathode 6 move into the luminescence layer 4 through the electron injection/transportation layer 5. As a result, the holes and electrons recouple in the luminescent layer 4, and the pre-scribed luminescence is released from luminescent layer materials in an excited state through the anode 2 and the substrate 1. Dependently upon the structures and ratio of the amine compound and the host and guest compounds to be used in combination, the organic EL device of this invention usually has a maximum for luminescence such as fluorescence at a wavelength of 500 to 650 nm in the green to red region. The x value for such luminescence is usually in the range of 0.01 to 0.73, and the y value, in the range of 0.26 to 0.83 on the xy chromaticity diagram established by the International Commission on Illumination (CIE).

The organic EL device of this invention would find a variety of uses in information displaying equipments to visualize information, for example, those in images and words and also in light sources or luminous bodies in illuminants in general because it is superior in durability, high in emission efficiency and as a result open to the elevation of brightness while suppressing its power consumption. Particularly, in the information displaying equipments, the organic EL device of this invention can be prepared into light panels with a desired form and size in usual manner to apply it to electric machine apparatuses, electronic- and optical-equipments in general to be required for a visualized display of information, such as video displays in computer-related apparatuses, televisions, telephones, computerized game consoles, calculators, cameras, clocks, car navigation systems; measuring instruments in general; signs; signboards; and advertising panels, which are directed to uses at home and professional uses. In such a case, the organic EL device of this invention may be driven by applying thereto a driving circuit of conventional simple or active matrix type usually used in this art while using it alone or combining with other organic EL devices which emit a visible light in the blue, green and/or red region and appropriate filters to control luminescent chromaticity and color tone, if necessary. In case of using in illuminants, the organic EL device of this invention is prepared into a light panel with a desired form and size in usual manner so that it is feasible as energy- and space-saving light source in illuminants in general such as interior or exterior illuminations, backlights for liquid crystal elements, illuminants usable to physical medicines for treating depression, and illuminants for controlling photoperiodism and phototaxis in animals and plants such as farm animals, poultry, fish and shellfish, insects, fruit trees, cereals, vegetables, and flowers and ornamental plants. Organic EL devices according to this invention, using in the anode and cathode a set of reflecting mirrors which function as optical microcavity, are useful in, for example, non-threshold lasers operable in a less current region.

By the way, since, as described heretofore, the amine compound of this invention has an absorption maximum at a wavelength region around 300 to 500 nm, usually, around 400 to 470 nm, and a large molecular absorption coefficient of $1\times10^4$ or larger, preferably, $3\times10^4$ or larger, it is useful as chromaticity controlling material to modify the chromaticity of luminescence from organic EL devices to a desired level, in addition to as luminescent layer material in organic EL devices. Thus, the term "organic EL device" as referred to as in this invention includes organic EL devices in general where with the purpose of controlling the chromaticity of electroluminescence from luminescent compounds, the specific amine compound is used alone or in combination with one or more other compounds with a light-absorbing ability in a part other than the luminescent layer, in addition to those which comprise the specific amine compound as luminescent layer material.

Several embodiments according to this invention will be explained with reference to Examples.

EXAMPLE 1

Amine Compound 50 ml of toluene were placed in a reaction vessel, admixed with 2.50 g of N,N'-diphenylbenzidine, 6.86 g of the coumarin compound represented by Chemical Formula 51, 0.17 g of palladium acetate, 2.0 g of potassium tert-butoxide, and 0.36 ml of tri-tert-butylphosphine, and reacted for four hours under reflux conditions. The reaction mixture was cooled, and purified on column chromatography using chloroform/ethyl acetate as eluent, thus obtaining 3.20 g of the amine compound of this invention represented by Chemical Formula 29 in a yellow powdery crystal form.

Chemical Formula 51:

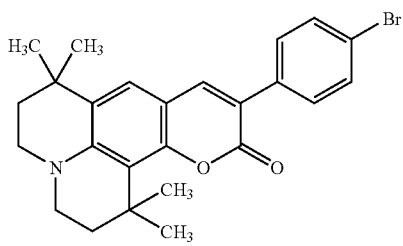

A part of the crystals was sampled, and its visible absorption and fluorescence emission spectra were determined in methylene chloride solution in usual manner, leading to the observation of absorption and fluorescence maxima at wavelengths around 427 ($\epsilon=9.18\times10^4$) and 512 nm, respectively. The amine compound of this Example showed a melting point around 368° C., glass transition point around 204° C., and decomposition point around 458° C. when determined by usual DSC analysis. The $^1$H-nuclear magnetic resonance spectrum (abbreviated as "$^1$H-NMR spectrum" hereinafter) in chloroform deuteride solution showed peaks at chemical shifts δ (ppm, TMS) of 1.31 (12H, s), 1.59 (12H, s), 1.75 to 1.84 (8H, m), 3.20 to 3.23 (4H, m), 3.27 to 3.31 (4H, m), 7.02 to 7.07 (2H, m), 7.12 to 7.19 (12H, m), 7.25 to 7.31 (6H, m), 7.47 to 7.49 (4H,m), and 7.63 to 7.65 (4H, m) when determined in usual manner.

The amine compound of this Example, which has a superior thermal stability and emits a green fluorescence when excited, is very useful as luminescent agent alone or in combination with other host and guest compounds in organic EL devices.

EXAMPLE 2

Amine Compound

4-Methoxyaniline and the compound represented by Chemical Formula 52, in place of N,N'-diphenylbenzidine and the compound represented by Chemical Formula 51 respectively, were allowed to react similarly as in Example 1, thus obtaining the amine compound represented by Chemical Formula 2 in a yellow powdery crystal form.

Chemical Formula 52:

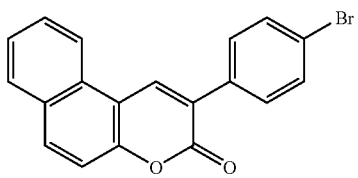

A part of the crystals was sampled, and its visible absorption and fluorescence emission spectra were determined in methylene chloride solution in usual manner, leading to the observation of absorption and fluorescence maxima at wavelengths around 415 ($\epsilon=4.06\times10^4$) and 562 nm, respectively. The amine compound of this Example showed a melting point around 305° C., glass transition point around 141° C., and decomposition point around 487° C. when determined by usual DSC analysis. The $^1$H-NMR spectrum in chloroform deuteride showed peaks at chemical shifts δ (ppm, TMS) of 3.78 (3H, s), 6.78 to 6.83 (4H, m), 7.22 to 7.27 (4H, m), 7.50 to 7.61 (4H, m), 7.68 to 7.77 (6H, m), 7.94 (2H, d), 7.98 (2H, d), 8.34 (2H, d), and 8.60 (2H, s) when determined in usual manner.

The amine compound of this Example, which has a superior thermal stability and emits a yellowish green fluorescence when excited, is very useful as luminescent agent alone or in combination with other host and guest compounds in organic EL devices.

EXAMPLE 3

Amine Compound

Aniline and the compound represented by Chemical Formula 52, in place of N,N'-diphenylbenzidine and the compound represented by Chemical Formula 51 respectively, were allowed to react similarly as in Example 1, thus obtaining the amine compound represented by Chemical Formula 3 in a yellow powdery crystal form.

A part of the crystals was sampled, and its visible absorption and fluorescence emission spectra were determined in methylene chloride solution in usual manner, leading to the observation of absorption and fluorescence maxima at wavelengths around 417 ($\epsilon=4.10\times10^4$) and 563 nm, respectively. The amine compound of this Example showed a melting point around 358° C., glass transition point around 153° C., and decomposition point around 495° C. when determined by usual DSC analysis. The $^1$H-NMR spectrum in chloroform deuteride solution showed peaks at chemical shifts δ (ppm, TMS) of 7.14 (2H, t), 7.24 to 7.37 (6H, m), 7.50 to 7.61 (4H, m), 7.68 to 7.77 (7H, m), 7.94 (2H, d), 7.99 (2H, d), 8.34 (2H, d), and 8.60 (2H, s) when determined in usual manner.

The amine compound of this Example, which has a superior thermal stability and emits a yellowish green fluorescence when excited, is very useful as luminescent agent alone or in combination with other host and guest compounds in organic EL devices.

EXAMPLE 4

Amine Compound

Either of three distinct amine compounds, obtained by the methods in Examples 1 to 3, was placed in a water-cooled sublimation purification apparatus and then heated in usual manner while keeping the inner space of the apparatus at a reduced pressure to effect sublimation purification.

The amine compounds in this Example are very useful in an organic EL device which requires a highly purified luminescent organic compound.

Although the amine compounds of this invention, including those represented by Chemical Formulae 1 to 50, are slightly different in starting reaction conditions and yields depending on their structures, they can be obtained by the methods in Examples 1 to 4 or in accordance therewith.

EXAMPLE 5

Organic EL Device

A multi-layer type of organic EL device with the structure of FIG. 1 was prepared by using an amine compound according to this invention as luminescent agent in organic EL devices. A glass substrate with a transparent ITO electrode, 160 nm thick, was patterned with a hydrobromic acid in usual manner, washed with organic alkali detergent, refined water, acetone and ethanol in the given order under ultrasonic conditions, dried, aerated with ultraviolet ozone to remove organic impurities from the surface of ITO electrode, and transferred to the pretreatment room in a vacuum depositing apparatus. The pretreatment room was then reduced to give an inner pressure of $1\times10^{-6}$ Torr, injected with a mixture of argon and oxygen gases to give an inner pressure of $1\times10^{-2}$ Torr, and subjected to plasma treatment, thus obtaining a clean substrate 1 with ITO electrode as the cathode 2.

The substrate 1 was transferred to the organic vaporizing room in the vacuum depositing apparatus which had been reduced to give an inner pressure of $1\times10^{-6}$ Torr, while the surface of ITO electrode as the cathode 2 was attached with an organic membrane-forming mask, after which the carbon crucible was heated to deposit triphenylamine tetramer represented by Chemical Formula 53 (abbreviated as "TPTE" hereinafter) as hole injection/transportation layer material to give a thickness of 40 nm, thus forming the hole injection/transportation layer 3. Subsequently, either of amine compounds of this invention represented by Chemical Formula 2 and 3 as host compound and 4-(dicyanomethylene)-2-tert-butyl-6-(1,1,7,7-tetramethyljulolidyl-9-enyl)-4H-pyran (abbreviated as "DCJTB" hereinafter), a red-light emitting dye, as guest compound were simultaneously deposited in a weight ratio of 100:1 to form the luminescent layer 4 with a thickness of 40 nm while allowing it to contact with the hole injection/transportation layer 3, after which aluminium tris (8-quinolinolate) (abbreviated as "AlQ$_3$" hereinafter) was deposited to form the electron injection/transportation layer 5 with a thickness of 40 nm while allowing it to contact with the luminescent layer 4.

Chemical Formula 53:

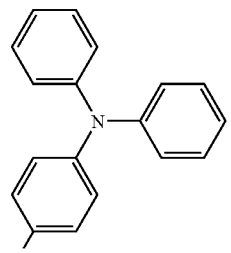

-continued

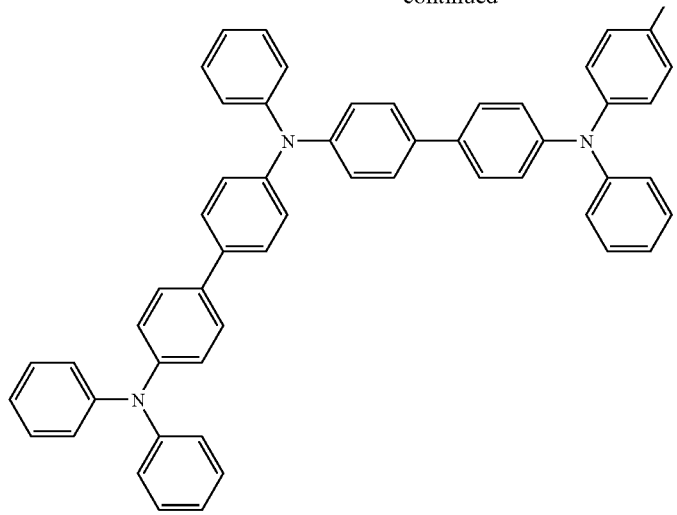

Chemical Formula 54:

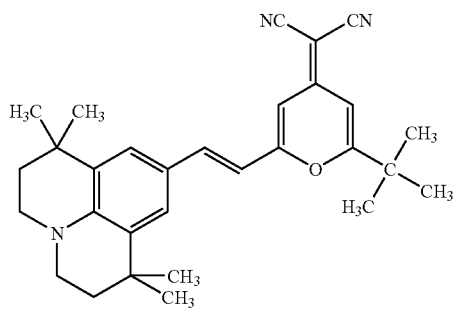

Thereafter, the substrate 1 was transferred to the metal-depositing room in the vacuum depositing apparatus, deposited with lithium fluoride and aluminium in this order to give respective thicknesses of 0.5 and 150 nm to form the anode 6 while allowing it to contact with the electron injection/transportation layer 5, after which the resultant was sealed with a glass plate and ultraviolet-setting resin under nitrogen-aerating conditions, thus obtaining organic EL devices. The organic EL devices thus obtained were determined in usual manner for electroluminescent properties and life expectancy (or a driving time to halve initial brightness). The life expectancy thereof was determined by setting the initial brightness to 2,400 cd/m² at room temperature. Separately, an additional organic EL device as control for comparison, where the amine compound of this invention was replaced with AlQ₃, a host compound extensively used in the art, was prepared and examined similarly as in the above. The results were as shown in Table 1.

TABLE 1

| Host compound | Guest compound | A | B | C | D | E | F | G | Remarks |
|---|---|---|---|---|---|---|---|---|---|
| Chemical Formula 3 | DCJTB | 5.8 | 627 | (0.65, 0.35) | 600 | 3.0 | 5.0 | 4,000 or over | Present invention |
| Chemical Formula 2 | DCJTB | 5.4 | 630 | (0.65, 0.35) | 547 | 2.9 | 4.8 | 1,000 or over | Present invention |
| AlQ₃ | DCJTB | 7.4 | 627 | (0.64, 0.35) | 236 | 0.9 | 1.9 | 18 | Control |

Note:
The symbols "A", "B", "C", "D", "E", "F", and "G" mean "Impressed voltage (V)", "Wavelength of luminescent maximum (nm)", "Chromaticity diagram (x, y)", "Luminescent brightness (cd/cm²)", "Electric power efficiency (lm/W)", "External quantum efficiency (%)", and "Life expectancy (hour)", respectively.

As seen from the results in Table 1, the organic EL devices of this Example and the control organic EL device commonly exhibited a luminescent maximum at a wavelength around 627 to 630 nm in the orange to red region. In the control organic EL device, the x value in color coordinates on the xy chromaticity diagram established by CIE was 0.64; and the y value, 0.35, while in the organic EL devices of this Example, the x and y value were 0.65 and 0.35, respectively. No luminescences inherent to the host compound were observed in the organic EL devices of this Example and control organic EL device, indicating that the excited energy was efficiently transferred from the host compound to the guest compound.

However, as seen in the column of "Luminescent brightness" in Table 1, when driven with a constant current of 11 mA/cm$^2$, the organic EL devices in this Example exhibited a brightness (547 cd/m$^2$ or over) exceeding 2-fold of that in control organic EL device at ambient temperature, and their electric powers and external quantum efficiencies were superior to those of the control organic EL device. In the organic EL devices in this Example, the electroluminescence consistently prolonged, and non-luminescent parts such as dark spot were not observed when driven with elevated brightness (2,400 cd/m$^2$) for 100 hours, while the control organic EL device had at most a life expectancy of 18 hours when tested similarly as above. The life expectancy for the organic EL device using the amine compound represented by Chemical Formula 3 was significantly long, and estimated to be 20,000 hours or over when driven with a practical brightness of 300 cd/m$^2$, confirming that it was not causative of any problems in practical use. The organic EL devices of this Example had a life expectancy of 700 hours or longer when driven by energizing them with a dc voltage slightly higher than 7V similarly as in energizing the control organic EL device.

These results demonstrate that the use of the amine compound according to this invention as luminescent agent realizes organic EL devices which give an emission in the orange to red region with a long life expectancy and high brightness and efficiency.

EXAMPLE 6

Display Panel

Figure 2:
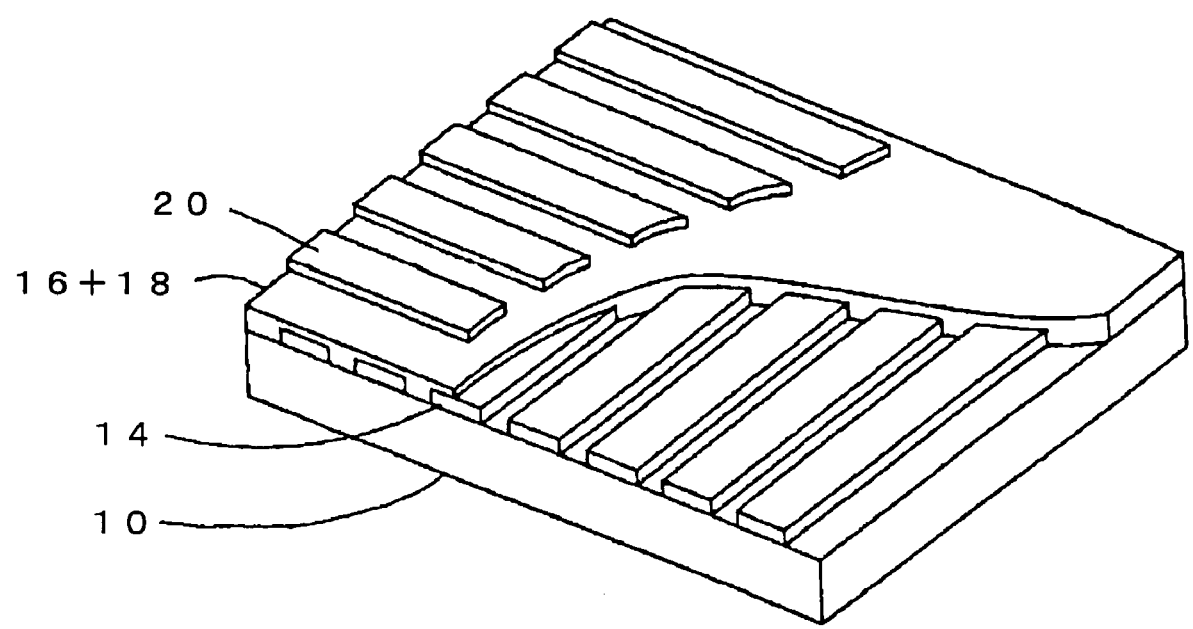
FIG. 2 is a brief figure of an example for display panel according to this invention.

FIG. 2 is a brief figure of a single matrix type display panel (20 stripes of electrodes in the row direction and 30 stripes of electrodes in the column direction) which comprises the organic EL device of this invention as substantial element: Such display panel can be prepared as follows.

The anode 14 of a transparent ITO electrode is formed on one side of the glass substrate 10 in accordance with the method in Example 5, and then striped by the wet-etching method. The hole injection/transportation layer 16 and luminescent layer 18 are formed in this order in accordance with the method in Example 5, and the cathode 20 is striped with a mechanical mask, followed by sealing the organic EL device with a glass plate (not given in the Figure) and ultraviolet-setting resin. In the display panel of this example, heat radiating means such as heat radiating plate and cooling fan may be provided on the backside of the cathode 20.

EXAMPLE 7

Information Displaying Equipment

Figure 3:
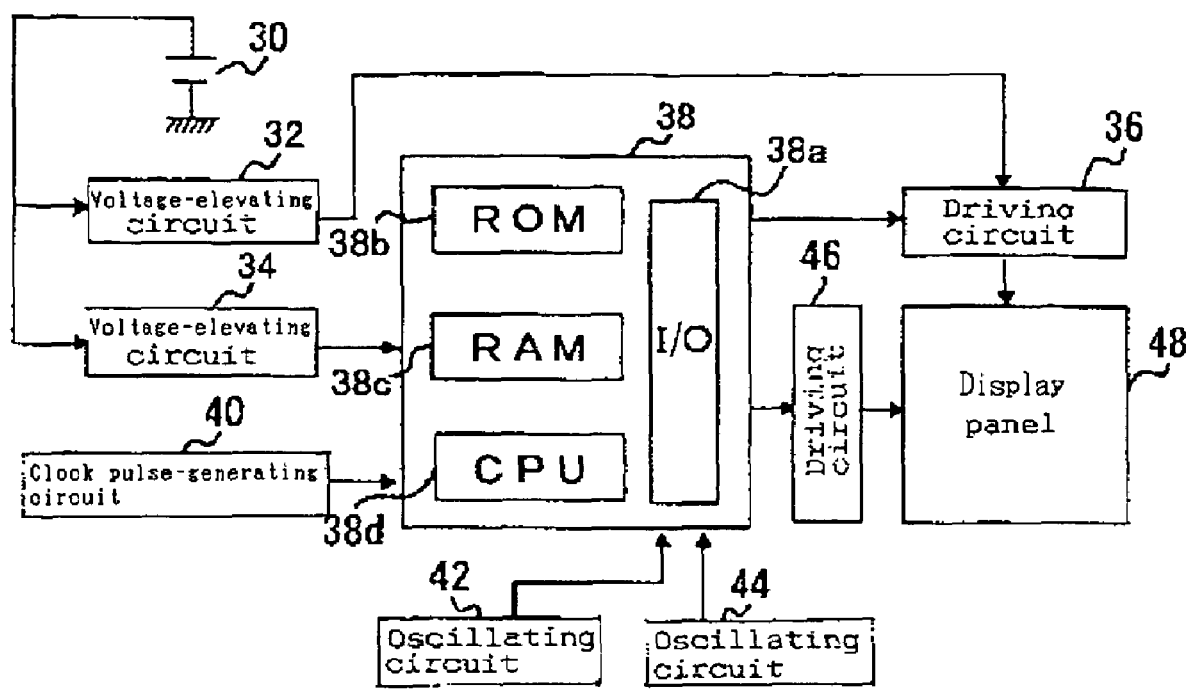
FIG. 3 is a brief figure of an example for information displaying equipment according to this invention.

FIG. 3 is a block diagram of an information displaying equipment which uses a display panel prepared by the method in Example 6. In FIG. 3, the reference numeral 30 represents a dc source, output voltage of 4.5 V, and its output terminals are connected with a pair of voltage-elevating circuits 32 and 34. The voltage-elevating circuit 32 is to supply a dc voltage of 5 to 12 V, and its output terminals are connected with the driving circuit 36. The other voltage-elevating circuit 34 is to supply a constant voltage of 5 V to the microcomputer 38.

The microcomputer 38 in FIG. 3 comprises the I/O interface 38a for exchanging signals with external sites, the ROM 38b for recording computer programs, the RAM 38c for recording data, and the CPU 38d for carrying out a variety of operations. To the microcomputer 38 is connected the clock pulse-generating circuit for supplying 8 MHz clock signal and the oscillating circuits 42 and 44 which are to supply 5 to 50 Hz signal to control the displaying speed and 0.2 to 2 kHz signal to control the scanning frequency, respectively.

The reference numeral 48 in FIG. 3 represents a display panel comprising the organic EL device of this invention as substantial element, which is connected with the microcomputer 38 through the driving circuits 36 and 46. The driving circuit 36 is to regulate the energization of dc voltage from the voltage-elevating circuit to the display panel 48, which comprises a plurality of transistors connected with either stripe of electrode in the column direction in the display panel 48. Thus, when either transistor in the driving circuit 36 is turned on, the stripes of electrodes in the column direction connected with the transistor is energized with the voltage from the voltage-elevating circuit 32. While, the driving circuit 46 comprises a plurality of transistors connected with either stripe of electrodes in the row direction in the display panel 48, and when either transistor in the driving circuit 46 is turned on, the stripe of electrodes in the row direction connected with the transistor is grounded.

Since the information displaying equipment in this Example is assembled in this way, when one transistor in the driving circuits 36 and another transistor in the driving circuit 46 are turned on in accordance with the instruction of the microcomputer 38, a prescribed voltage is energized between corresponding stripes of electrodes in both row and column directions in the display panel 48 to allow the organic EL device at the intersection to release a luminescence. Because of this, for example, when one stripe of electrodes in the row direction is chosen by appropriately controlling the driving circuit 36, the transistors connected with respective stripes of electrodes in the column direction are sequentially turned on while grounding the former stripe of electrodes: Thus, the chosen stripe of electrodes in the row direction is wholly scanned to display a prescribed picture element. The whole picture can be displayed by sequentially repeating such scanning in the column direction. Since the driving circuit 36 in this Example has a resistor which can supply data enough to operate one stripe of electrodes, it is desirable to drive transistors with the data recorded therein.

The information to be displayed is externally supplied in accordance with displaying rate and frequency, and alternatively supplied with the data from the ROM 38b where information with prescribed patterns such as those in words have been recorded in the ROM 38b. In the case of displaying television broadcast in the usual NTSC mode, the received signals are separated into horizontal and vertical synchronizing signals in correspondence with the horizontal and vertical frequencies according to the broadcasting standard, and the image signals are converted into digital signals which correspond to the pixel number in the display panel 48. Television broadcasts can be displayed on the display panel 48 by supplying these signals to the microcomputer 38 while appropriately synchronizing the signals.

INDUSTRIAL APPLICABILITY

As explained heretofore, this invention is based on the creation of a novel aromatic tertiary amine. Since the amine compound of this invention has an absorption maximum in the visible region and efficiently absorbs a visible light, as well as since such an amine compound usually has a luminescent maximum in the visible region and a satisfiable stability, and emits a visible light when excited, it is useful as light absorbing- or luminescent-agent in a variety of fields of, for example, photochemical polymerization, solar cell, optical filter, dyestuff, dye laser, and analysis which require organic compounds with such properties: Also is useful as luminescent agent such as host- or guest-compound to form the luminescent layer, in addition to as chromaticity controlling material to modify the chromaticity of electroluminescence in the field of organic EL device which has been highlighted as displaying device of the next generation.

The invention claimed is:

1. An amine compound bearing within the same molecule one or more atomic groups represented by General Formula 1, said amine compound having an absorption maximum at a wavelength of around 390 to 500 nm, a molecular absorption coefficient of $1\times10^4$ or larger, a fluorescence maximum at a wavelength of around 500 to 650 nm, a decomposition point exceeding 400° C., and a glass transition point of 110° C. or higher, said amine compound being obtainable by reacting a compound represented by General Formula 2 with a compound bearing within the same molecule an atomic group represented by General Formula 3;

General Formula 1:

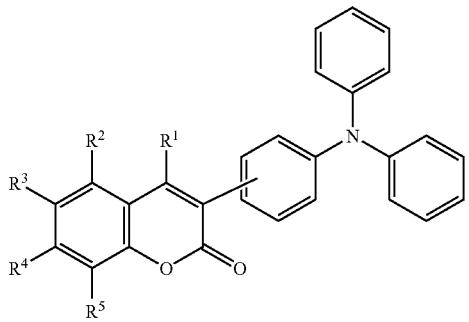

wherein in General Formula 1, (i) $R^1$ to $R^5$ independently denote a hydrogen atom or a substituent and optionally the neighboring two of $R^2$ to $R^5$ couple each other to form a cyclic structure, including the carbon atoms to which the neighboring two substituents are linked, said substituent being a member selected from the group consisting of aliphatic hydrocarbon groups, alicyclic hydrocarbon groups, aromatic hydrocarbon groups, ether groups, ester groups, amino groups, halogen groups, hydroxy group, carboxy group, cyano group, nitro group, and combinations thereof, with the proviso that, when the neighboring two of $R^2$ to $R^5$ couple each other to form a cyclic structure, including the carbon atoms to which the neighboring two substituents are linked, said substituent being a member selected from the group consisting of aliphatic hydrocarbon groups, alicyclic hydrocarbon groups, aromatic hydrocarbon groups, ether groups, ester groups, and combinations thereof; (ii) one, two or three coumarin residues directly or indirectly bind to a benzene ring(s) in the triphenylamino group at the para position(s) against the nitrogen atom in the tertiary amino group; and (iii) a part or whole benzene rings, which are bound to the nitrogen atom to form the tertiary amine group, are optionally either bound with one or more substituents corresponding to those in $R^1$ to $R^5$, or allowed to share a part of condensed polycyclic aromatic hydrocarbon groups or heterocyclic groups, General Formula 2:

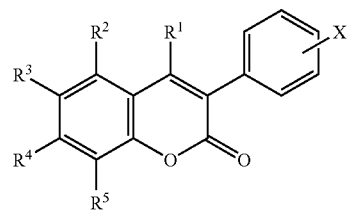

wherein in General Formula 2, $R^1$ to $R^5$ are substituents corresponding to those in General Formula 1, X denotes a halogen group, General Formula 3:

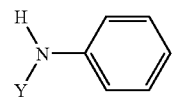

wherein in General Formula 3 Y denotes either of hydrogen atom, independent phenyl group or benzene ring which shares a part of a condensed polycyclic aromatic hydrocarbon or heterocyclic group.

2. The amine compound of claim 1, which is a member selected from the group consisting of:

Chemical Formula 1:

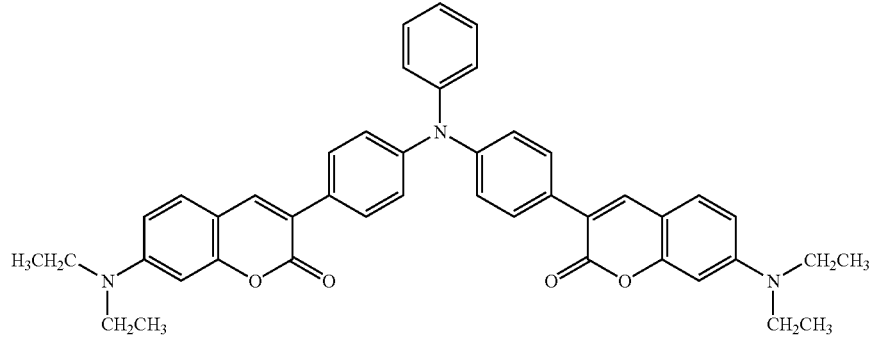

-continued
Chemical Formula 2:
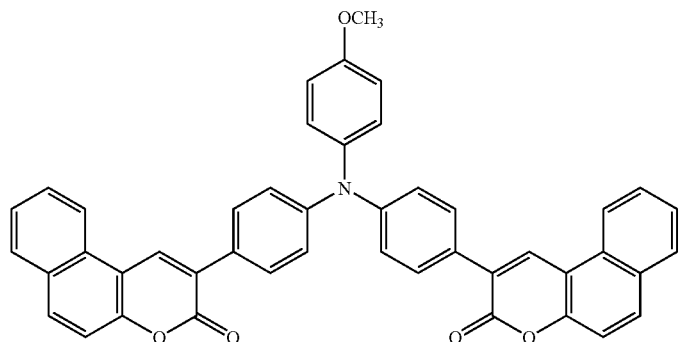
Chemical Formula 3:
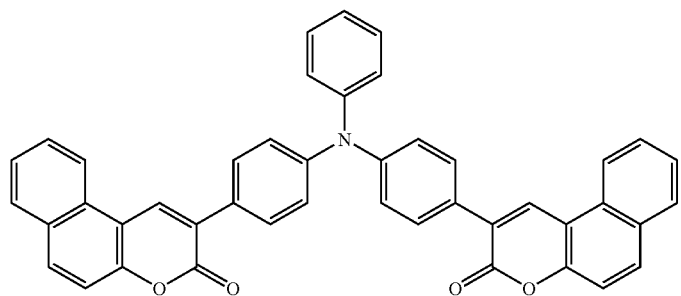
Chemical Formula 4:
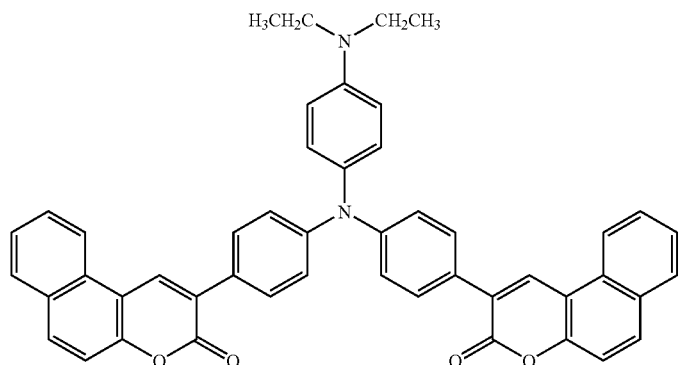
Chemical Formula 5:
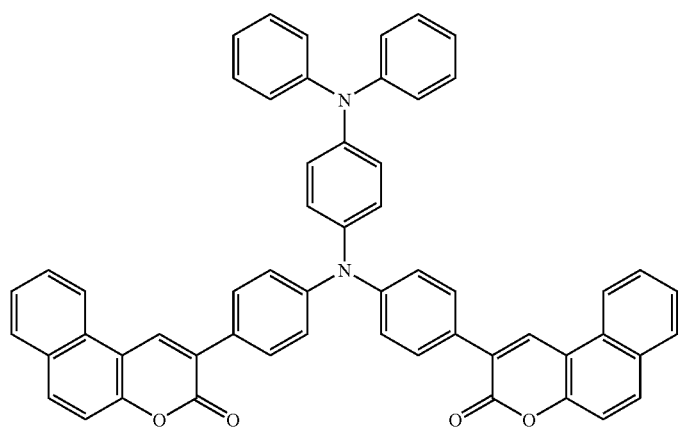

-continued
Chemical Formula 6:
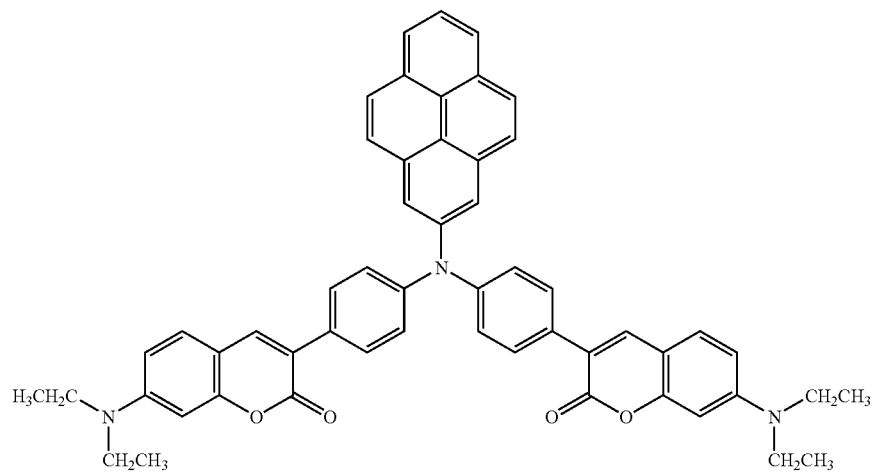
Chemical Formula 7:
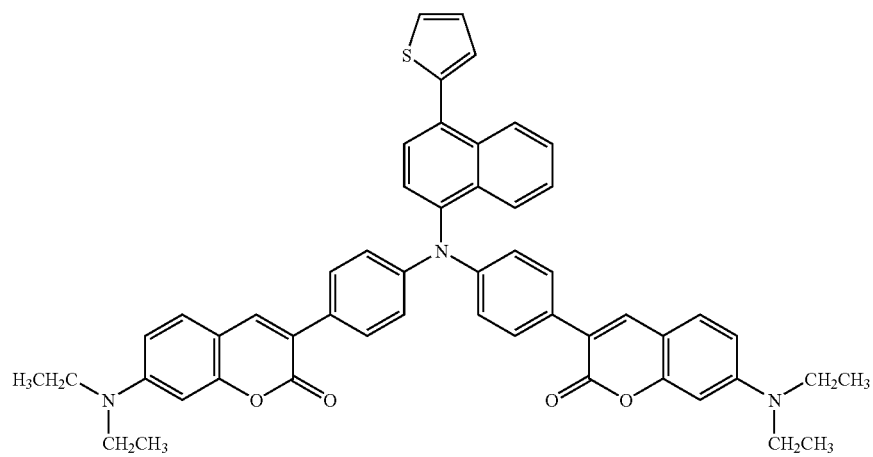
Chemical Formula 8:
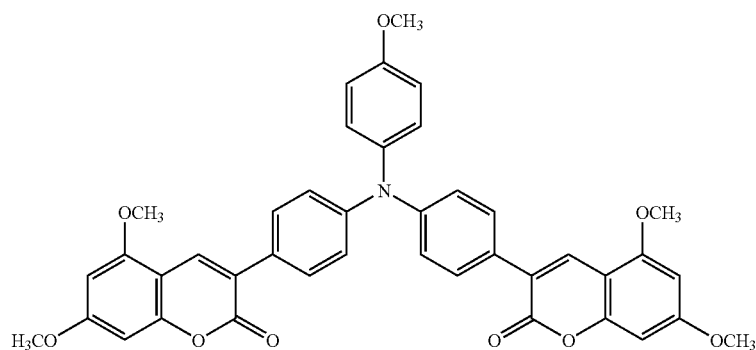

Chemical Formula 9:
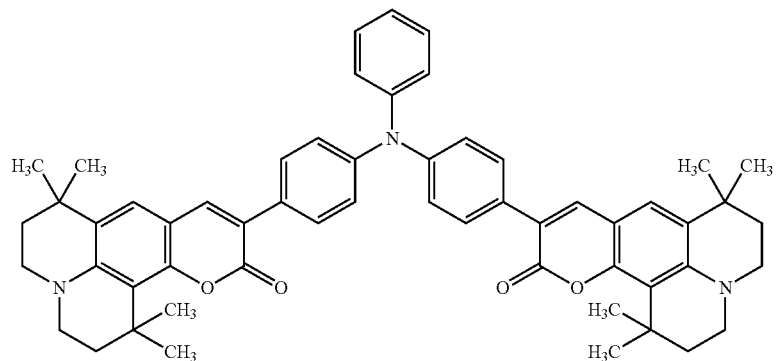
Chemical Formula 10:
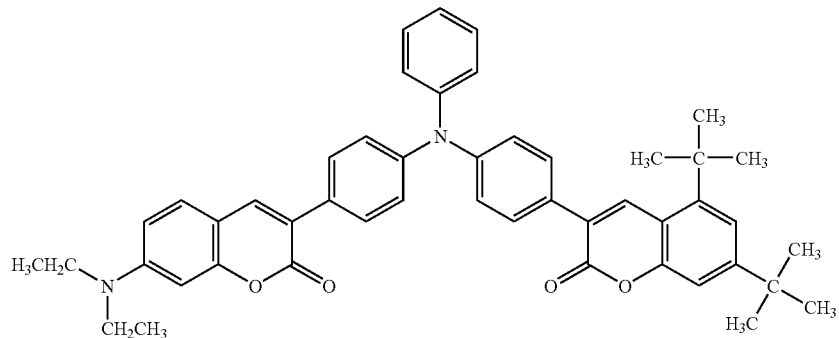
Chemical Formula 11:
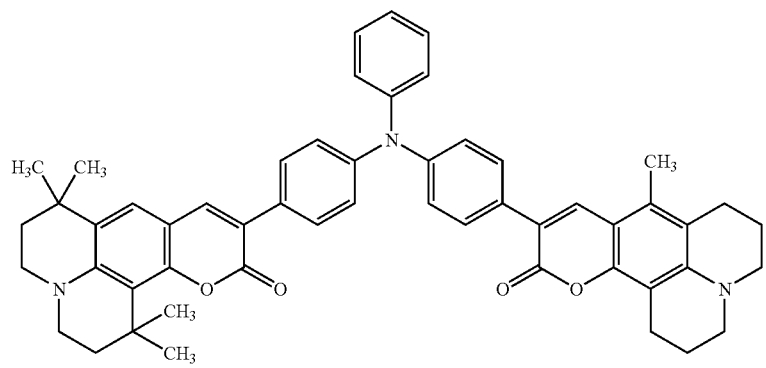

-continued
Chemical Formula 12:
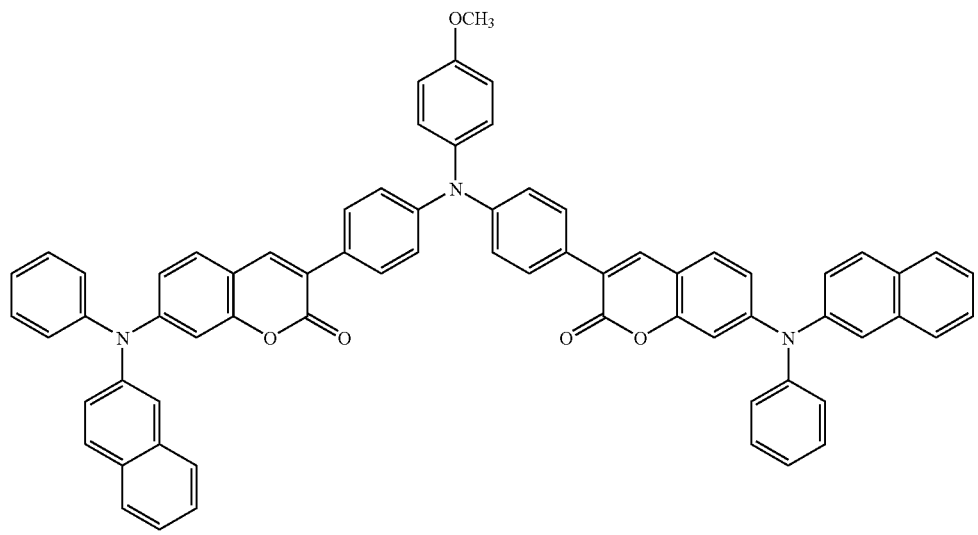
Chemical Formula 13:
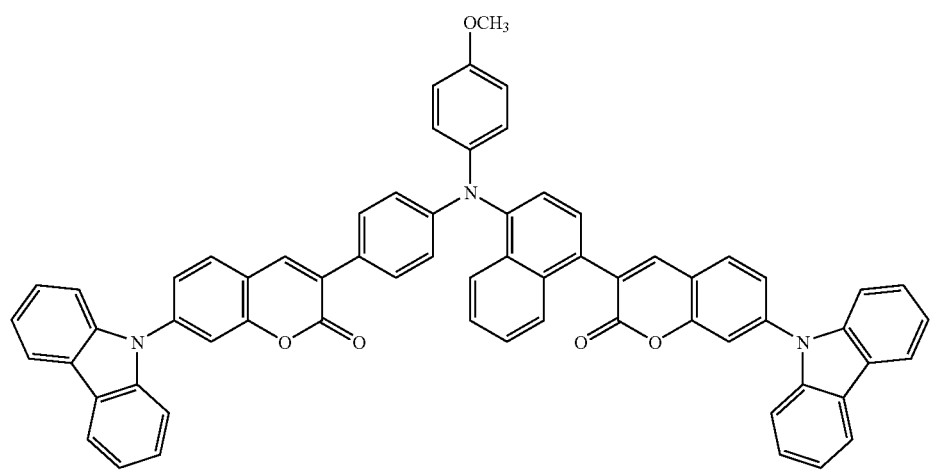
Chemical Formula 14:
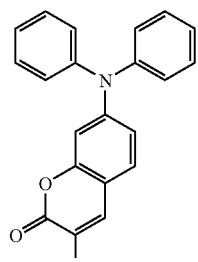

-continued
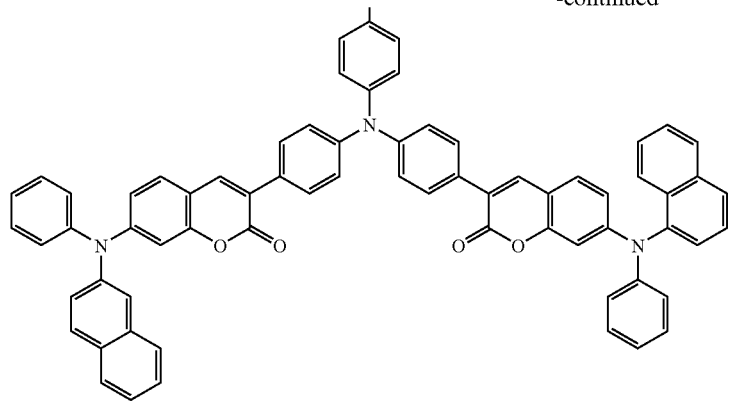
Chemical Formula 15:
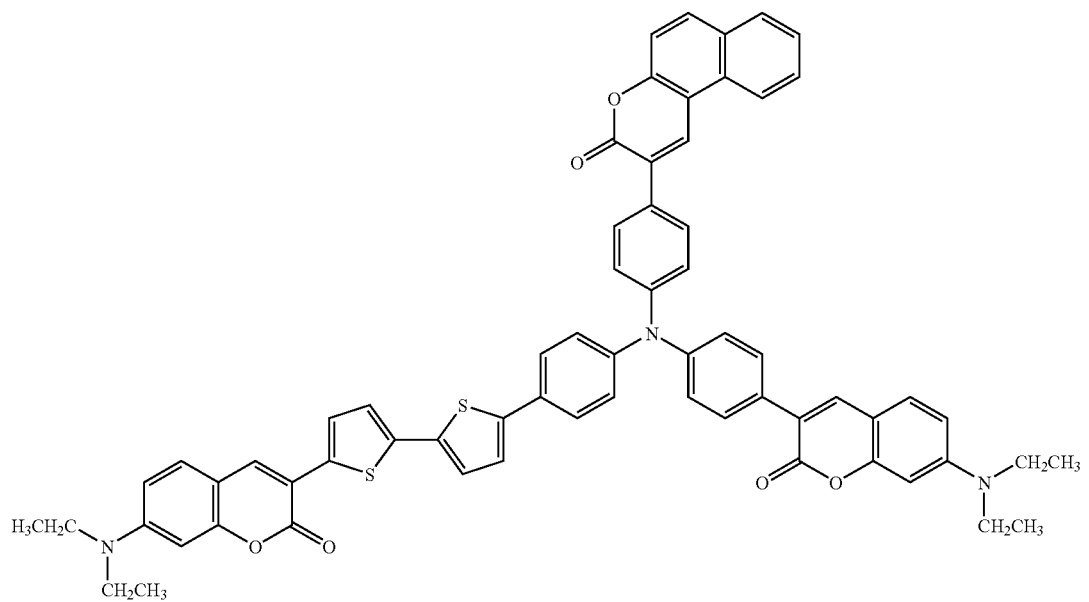
Chemical Formula 16:
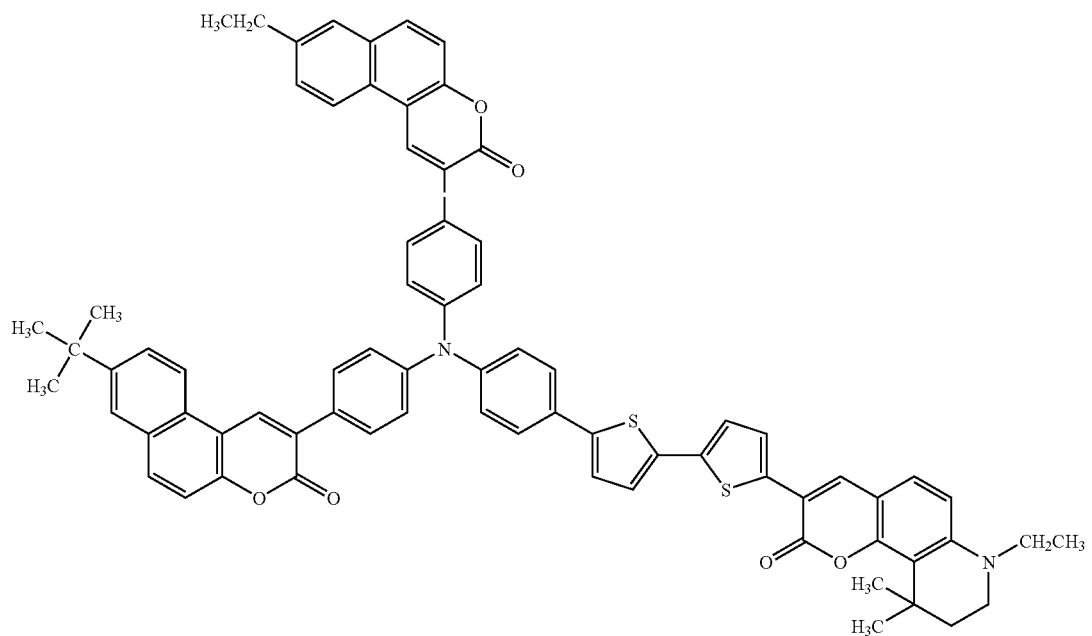

Chemical Formula 17:
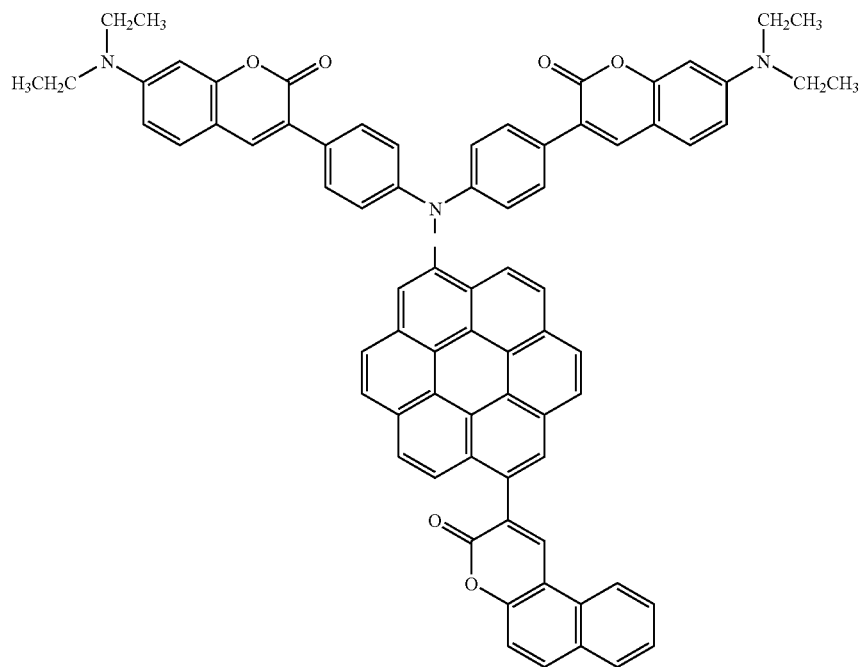
Chemical Formula 18:
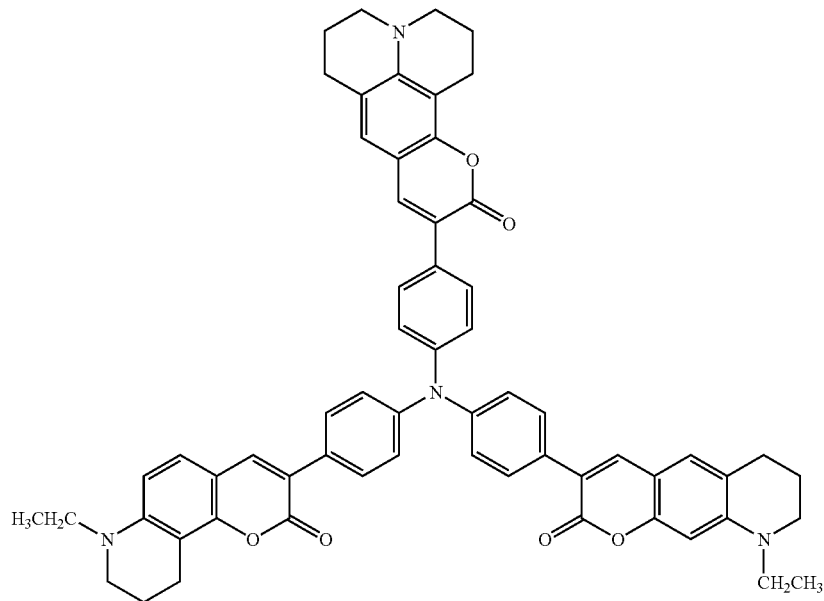
Chemical Formula 19:
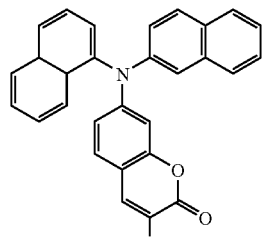

-continued
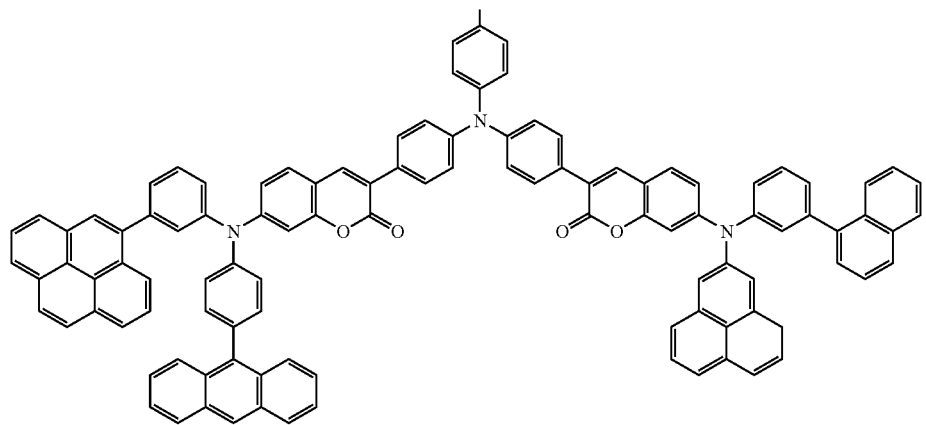
Chemical Formula 20:
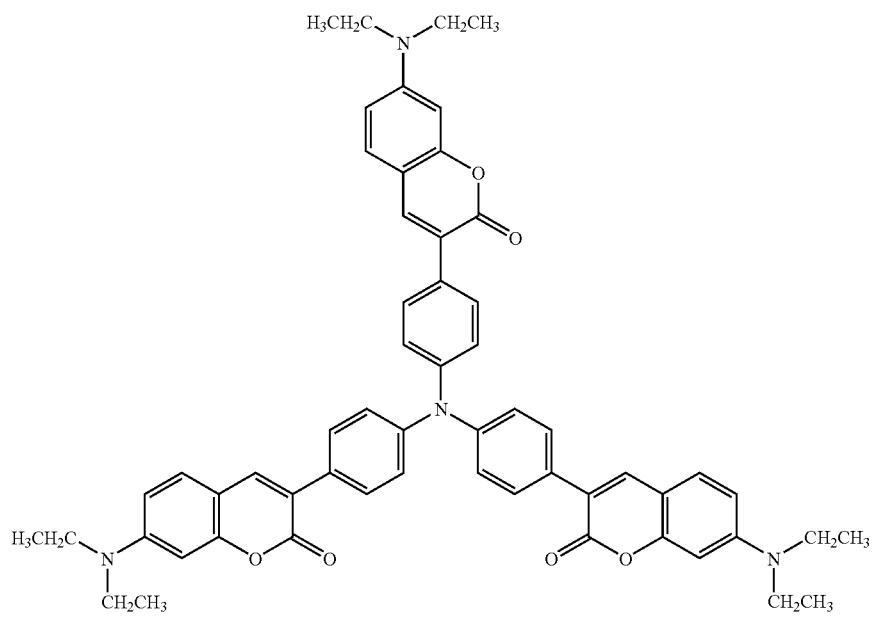
Chemical Formula 21:
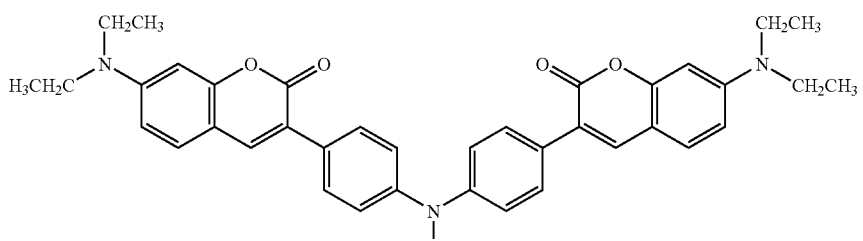

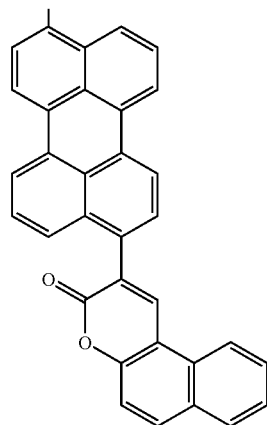
Chemical Formula 22:
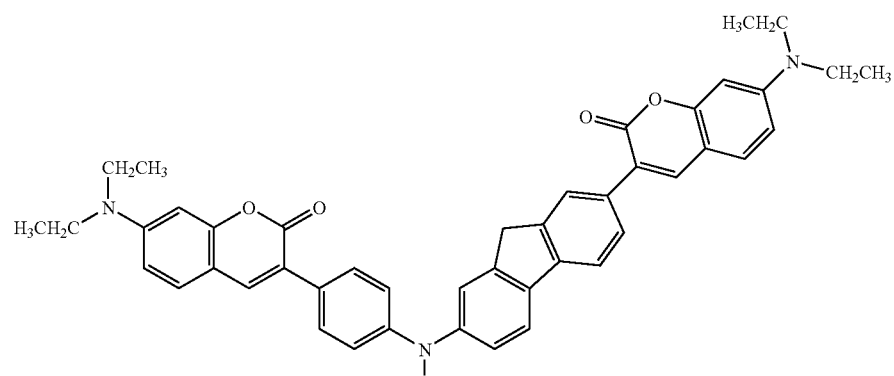
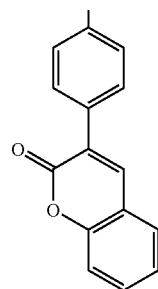
Chemical Formula 23:
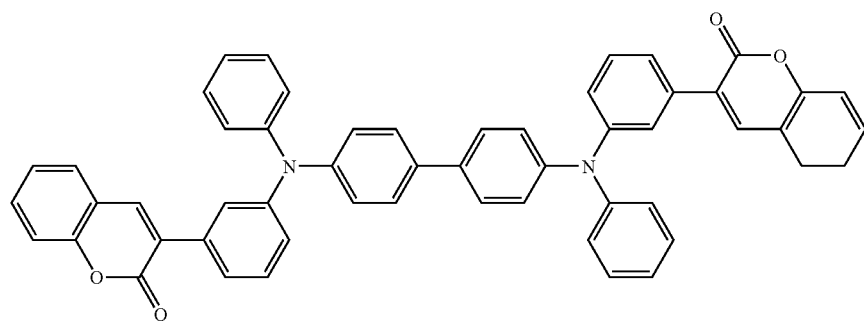

-continued
Chemical Formula 24:
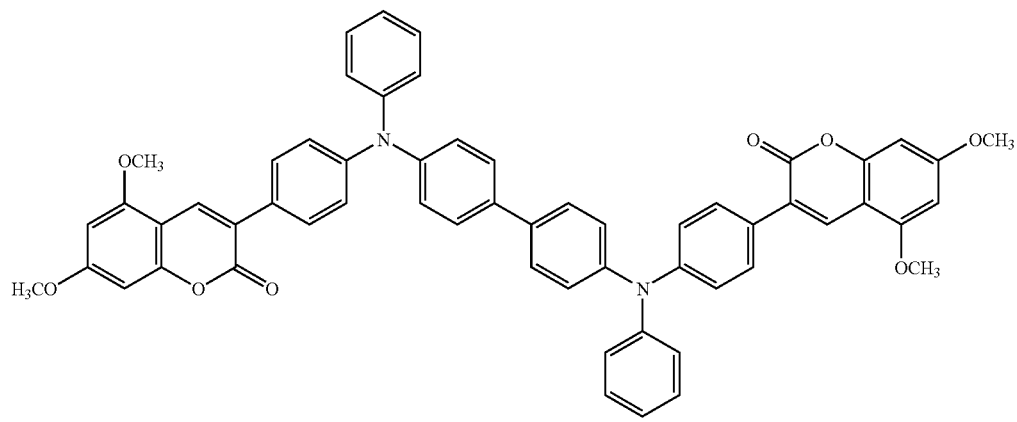
Chemical Formula 25:
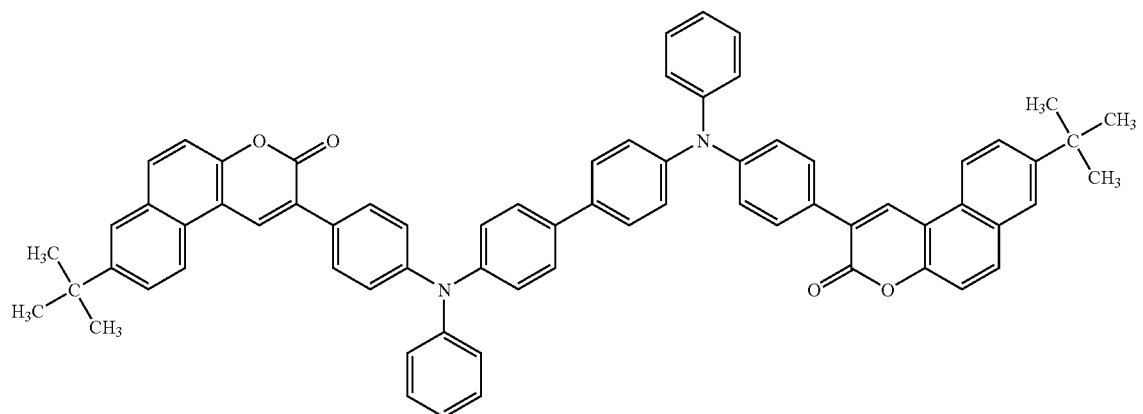
Chemical Formula 26:
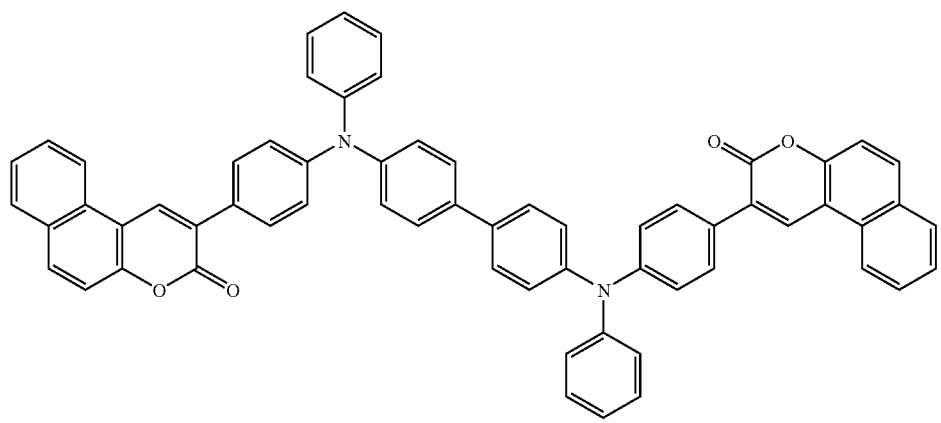

Chemical Formula 27:
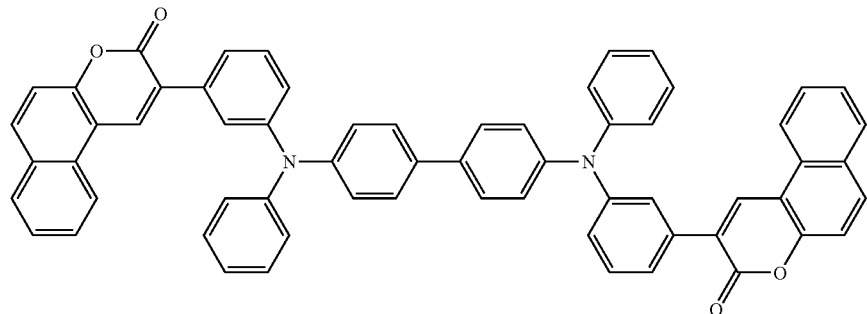
Chemical Formula 28:
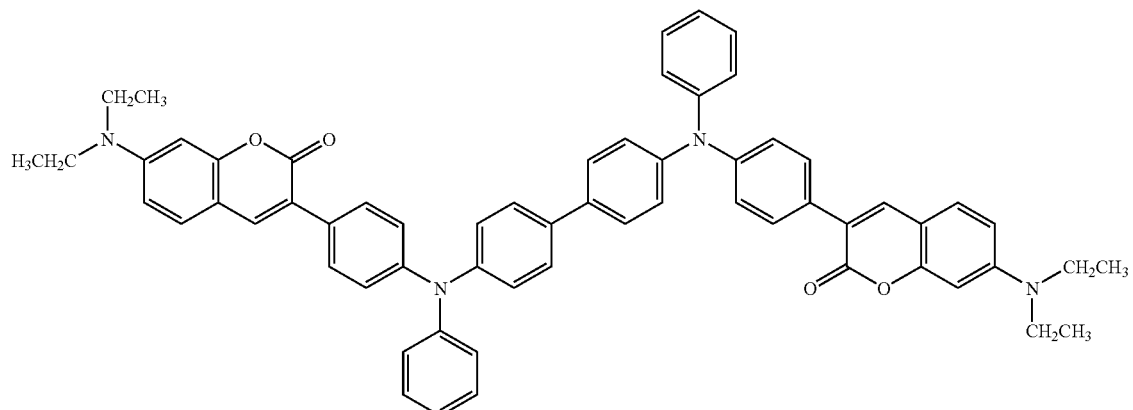
Chemical Formula 29:
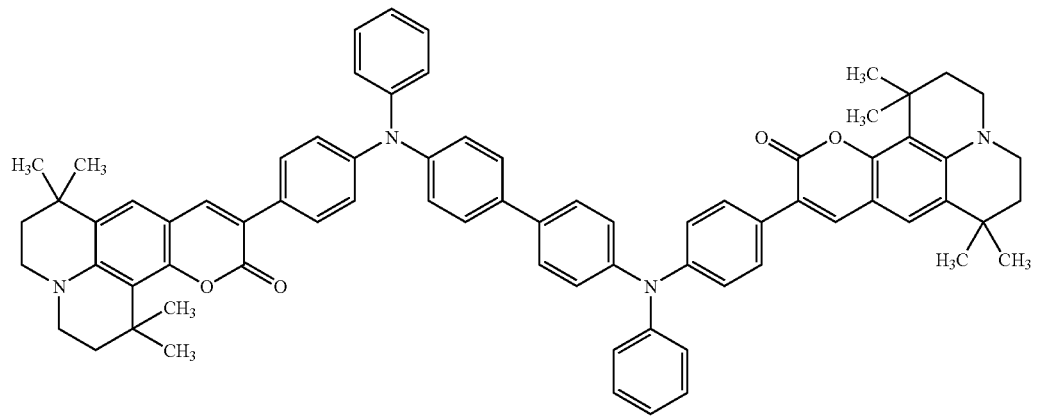
Chemical Formula 30:
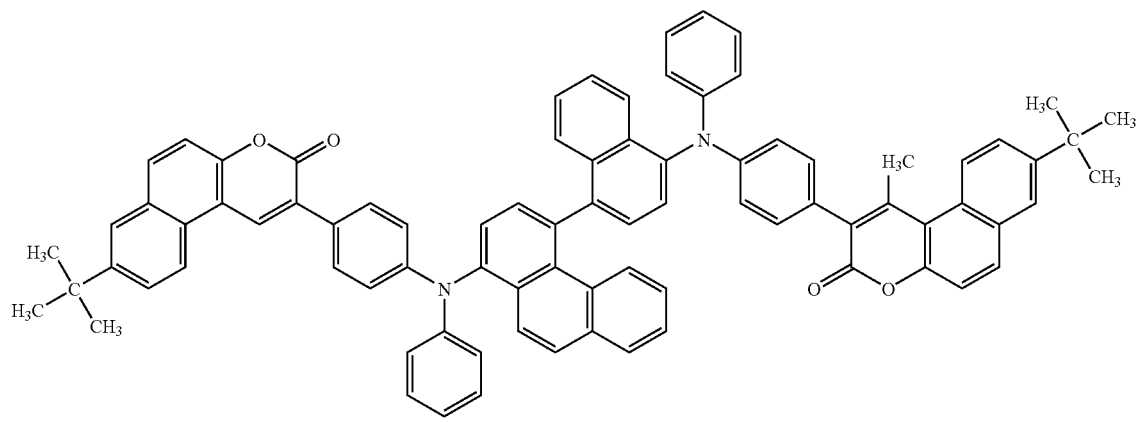

-continued
Chemical Formula 31:
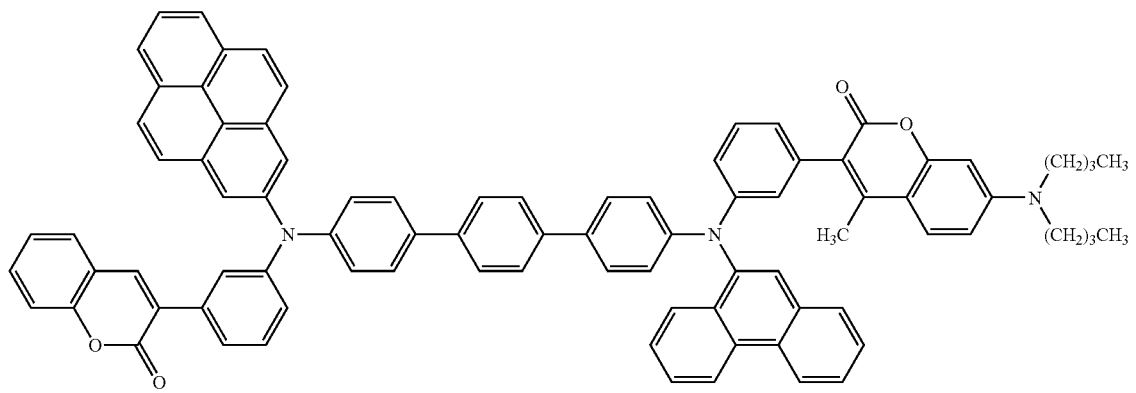
Chemical Formula 32:
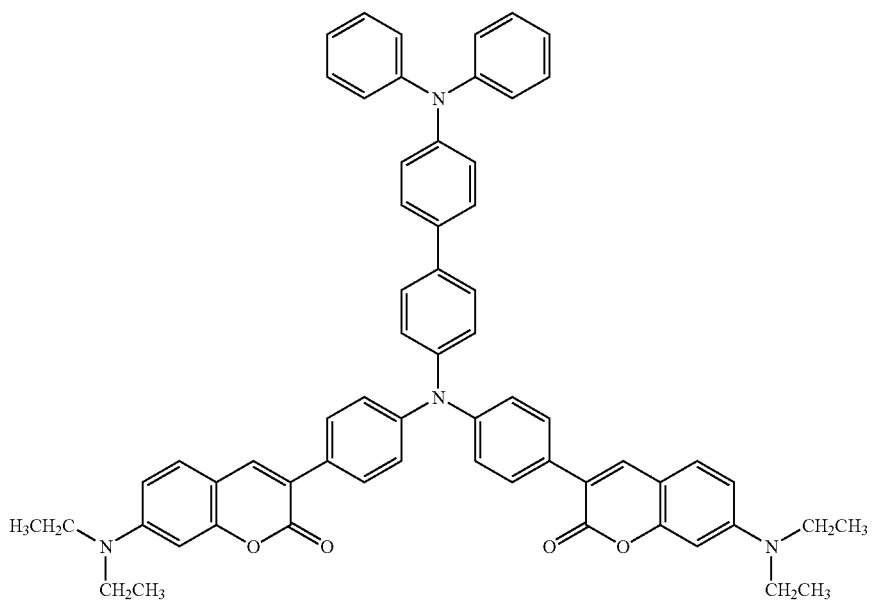
Chemical Formula 33:
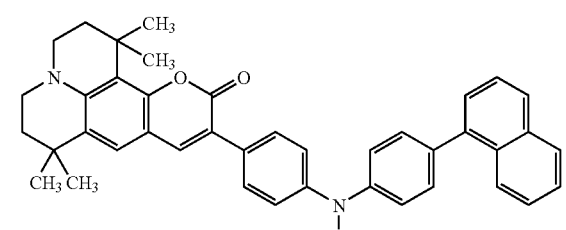

-continued
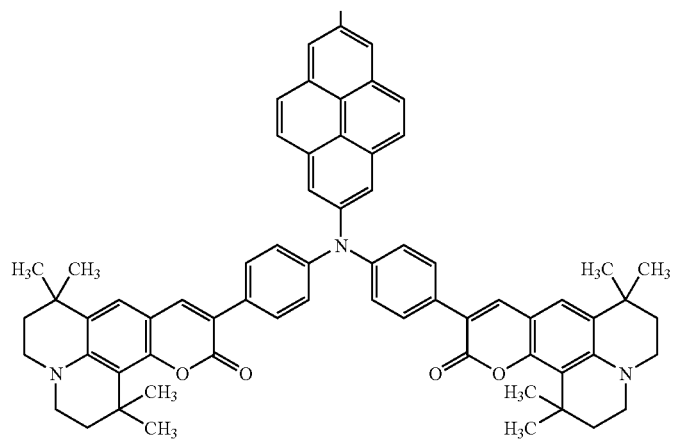
Chemical Formula 34:
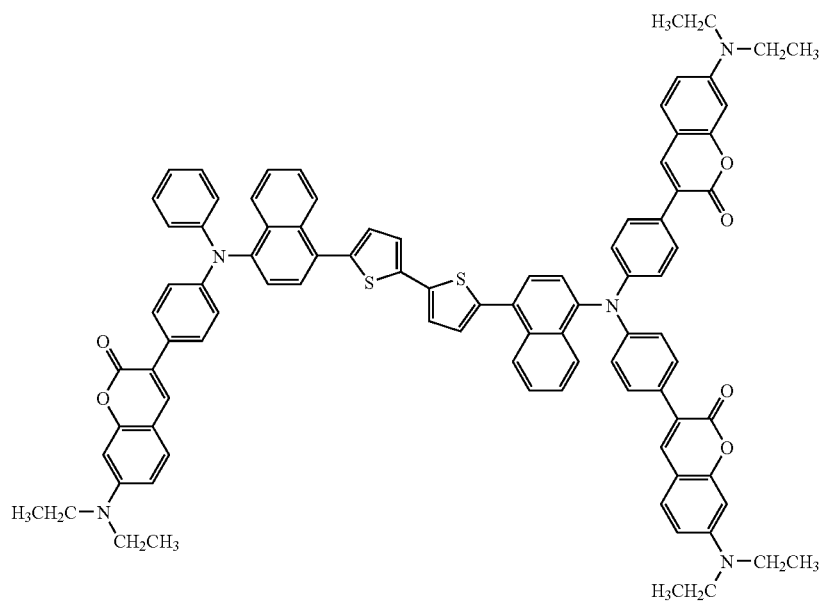
Chemical Formula 35:
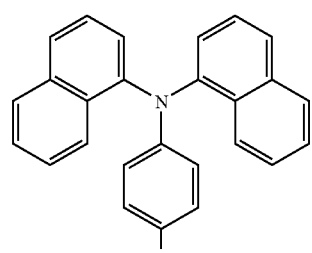

-continued
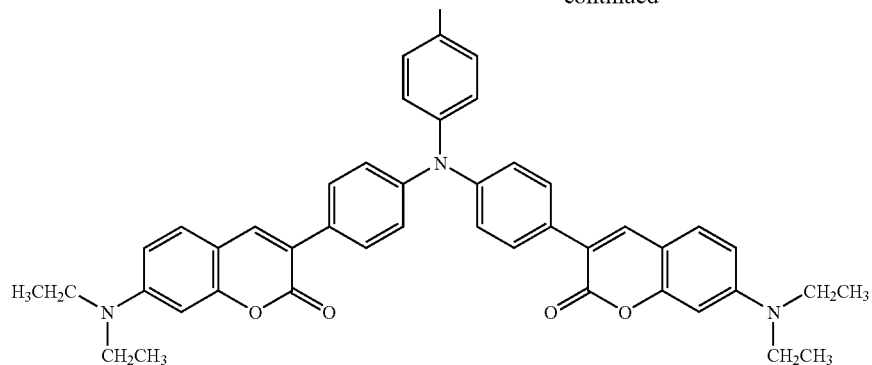
Chemical Formula 36:
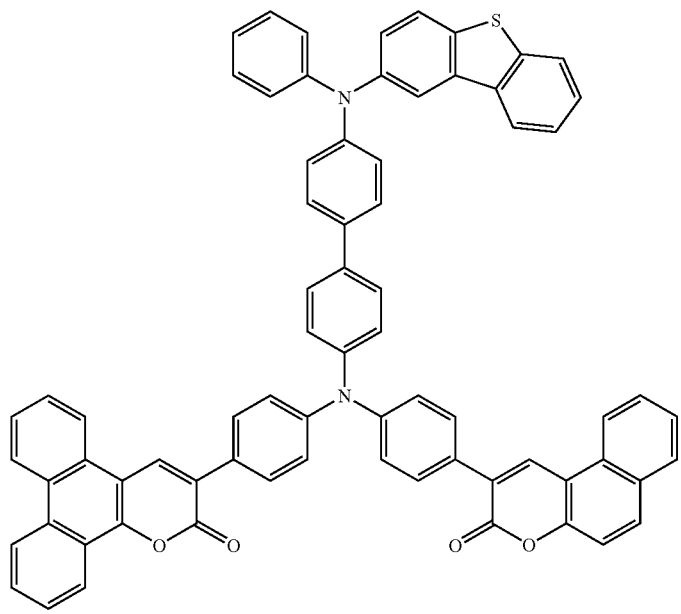
Chemical Formula 37:
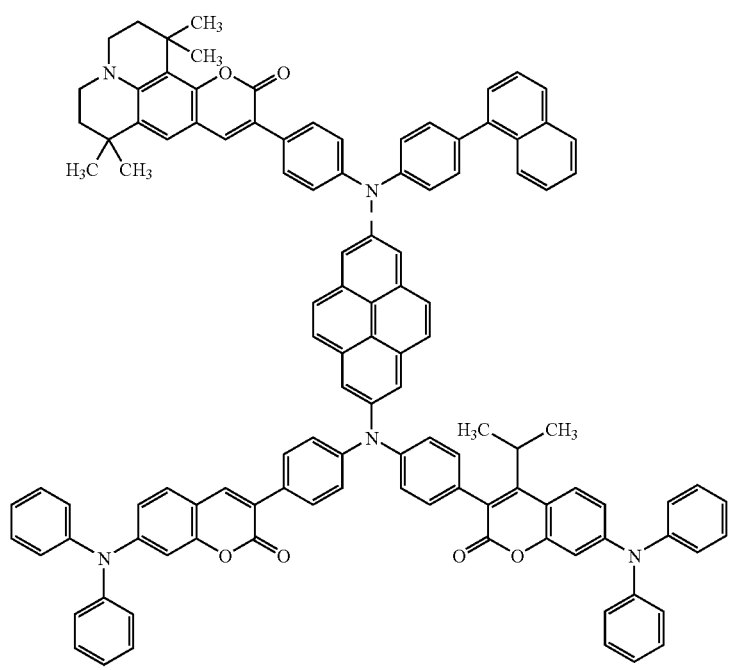

Chemical Formula 38:
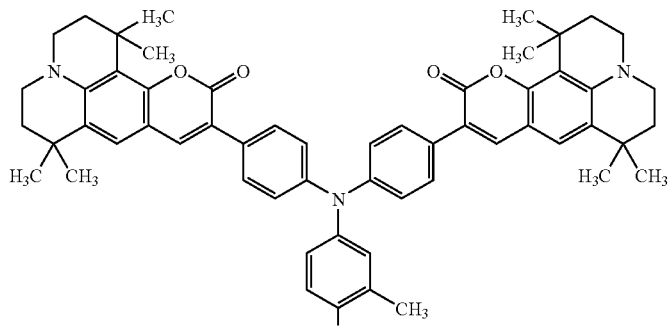
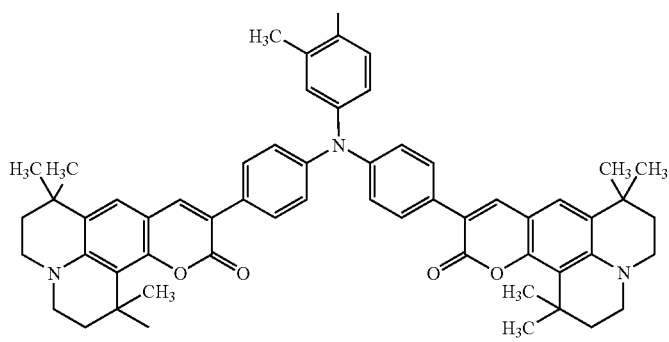
Chemical Formula 39
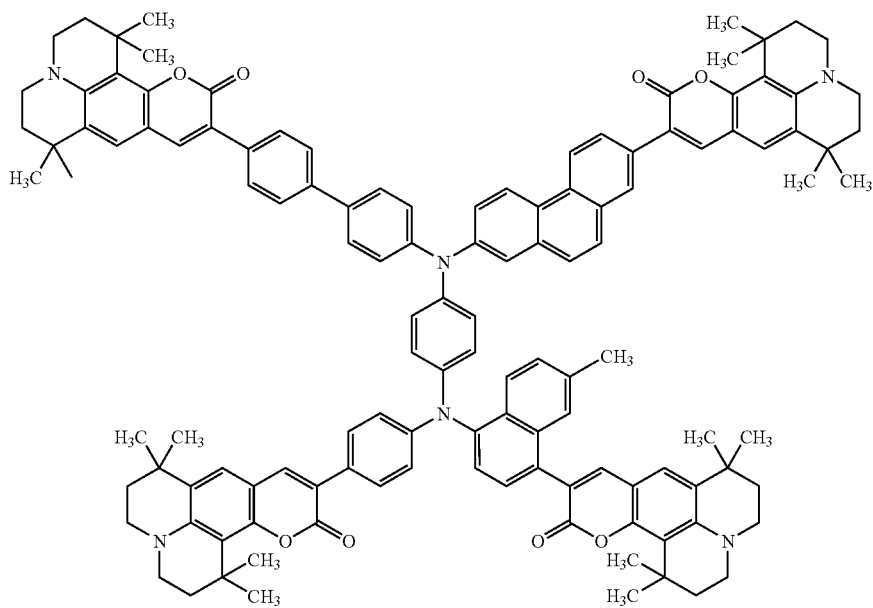

Chemical Formula 40:
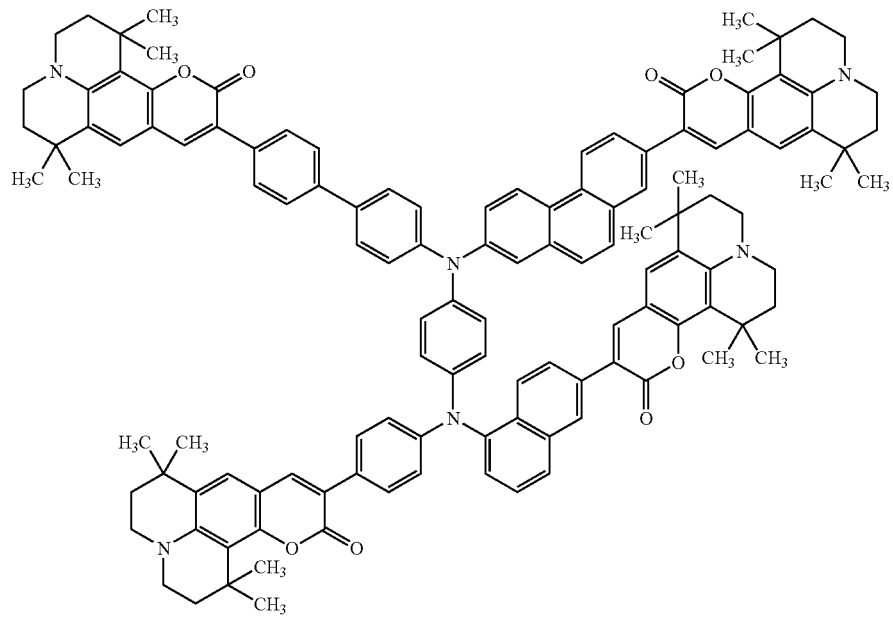
Chemical Formula 41:
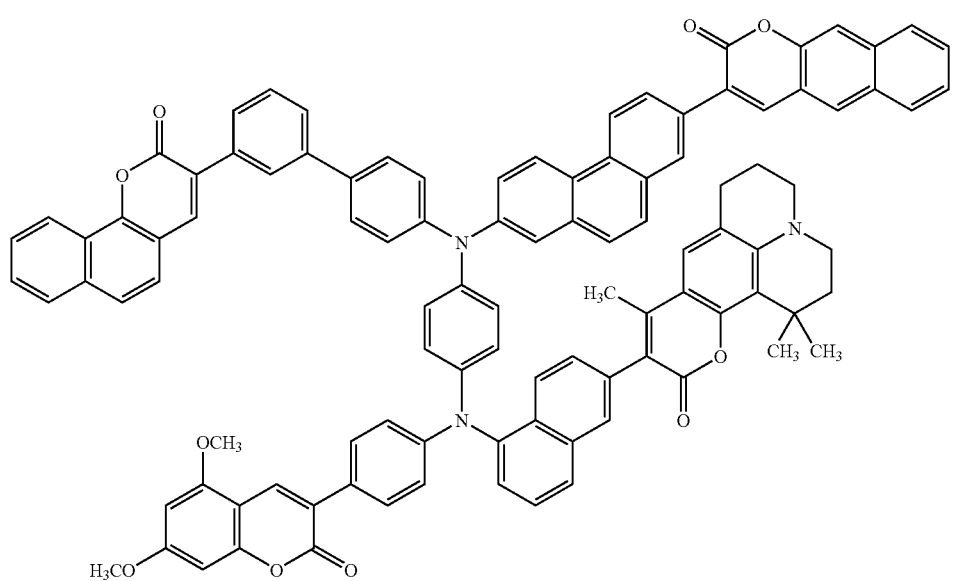

-continued
Chemical Formula 42:
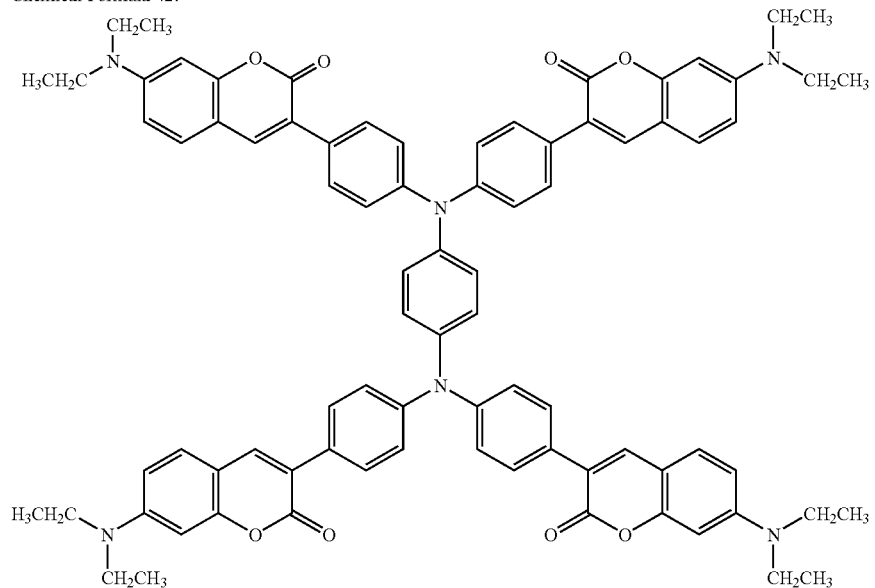
Chemical Formula 43:
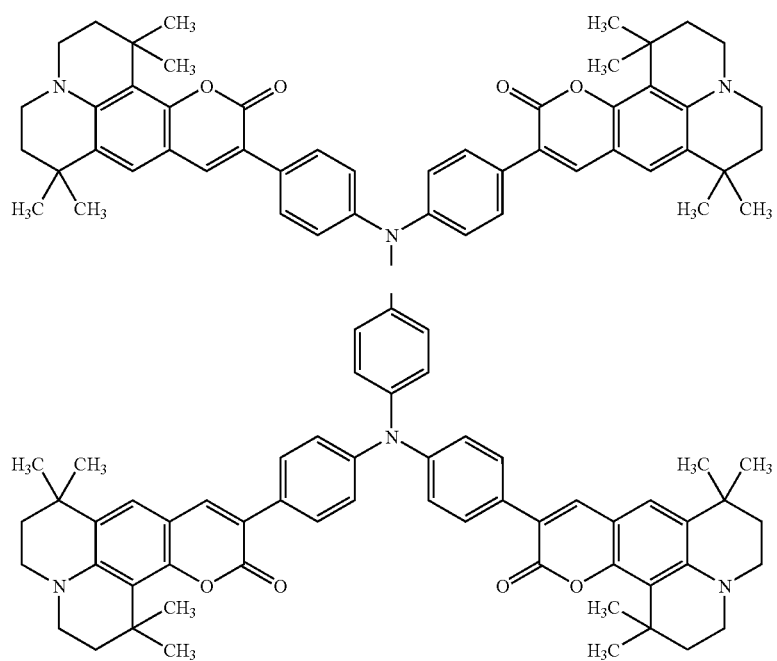
Chemical Formula 44:
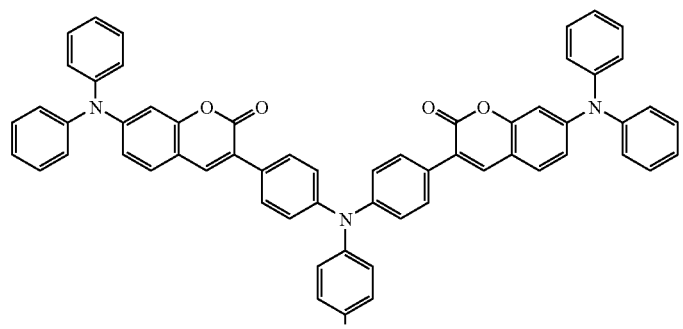

-continued
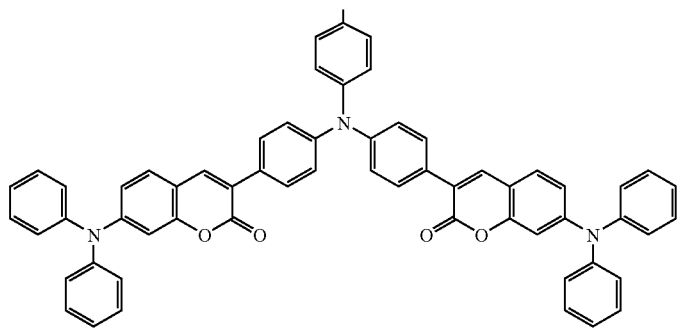
Chemical Formula 45:
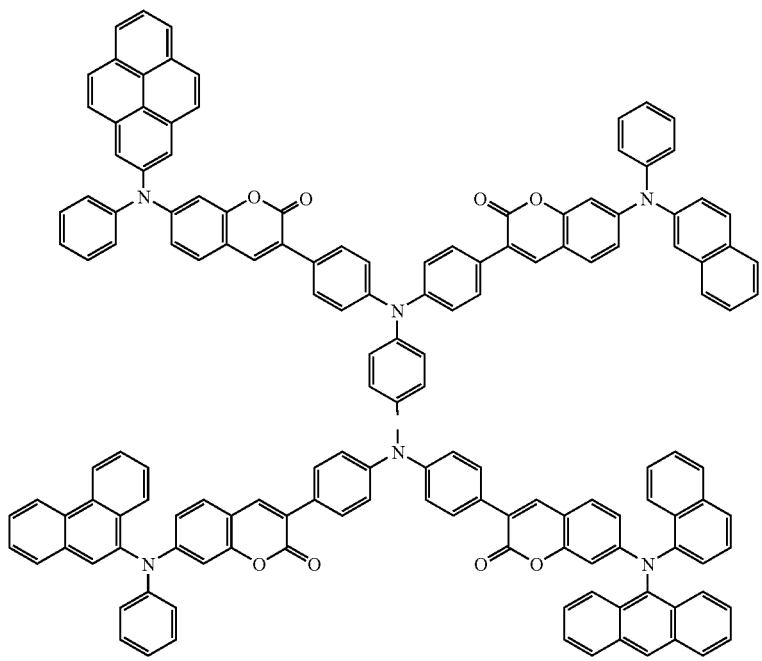
Chemical Formula 46:
Chemical Formula 47:
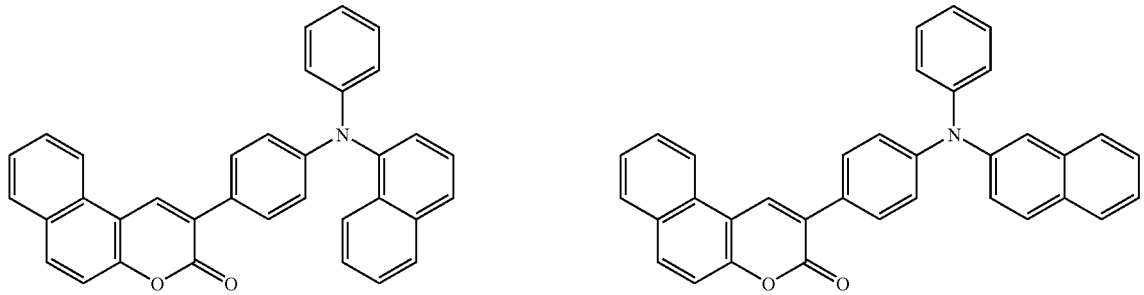
Chemical Formula 48:
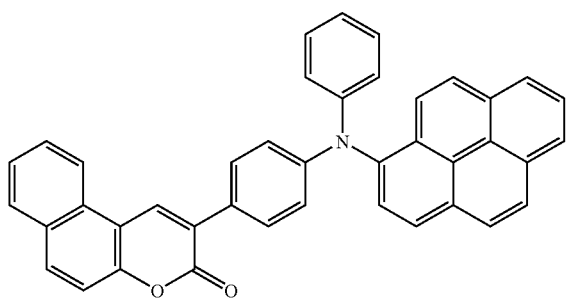

-continued
Chemical Formula 49:
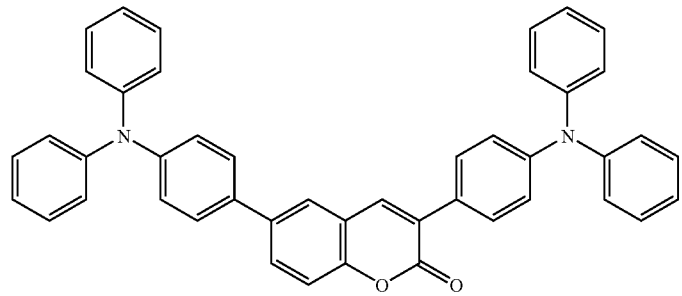
Chemical Formula 50:
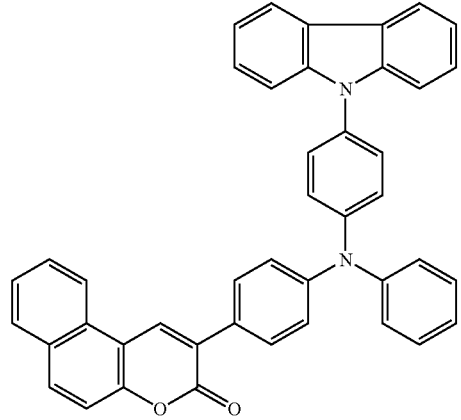
* * * * *